US009163198B2

(12) United States Patent
Oroskar et al.

(10) Patent No.: US 9,163,198 B2
(45) Date of Patent: Oct. 20, 2015

(54) PROCESS FOR PURIFICATION OF EPA (EICOSAPENTANOIC ACID) ETHYL ESTER FROM FISH OIL

(71) Applicant: OROCHEM TECHNOLOGIES, INC., Naperville, IL (US)

(72) Inventors: Anil R. Oroskar, Oak Brook, IL (US); Krishna Nagarajan Gopal, Naperville, IL (US)

(73) Assignee: OROCHEM TECHNOLOGIES, INC., Naperville, IL (US)

( * ) Notice: Subject to any disclaimer, the term of this patent is extended or adjusted under 35 U.S.C. 154(b) by 0 days.

(21) Appl. No.: 14/158,499

(22) Filed: Jan. 17, 2014

(65) Prior Publication Data

US 2015/0203789 A1   Jul. 23, 2015

(51) Int. Cl.
*C11C 3/00* (2006.01)
*C11B 7/00* (2006.01)
*B01D 15/18* (2006.01)

(52) U.S. Cl.
CPC ............ *C11C 3/003* (2013.01); *B01D 15/1821* (2013.01); *C11B 7/0058* (2013.01)

(58) Field of Classification Search
None
See application file for complete search history.

(56) References Cited

U.S. PATENT DOCUMENTS

| 4,792,418 | A | | 12/1988 | Rubin | |
|---|---|---|---|---|---|
| 5,171,870 | A | * | 12/1992 | Kulpraghipanja | ............ 554/193 |
| 5,175,324 | A | * | 12/1992 | Kulprathipanja | ............ 554/193 |
| 5,225,580 | A | * | 7/1993 | Zinnen | ............. 554/30 |
| 5,719,302 | A | * | 2/1998 | Perrut et al. | ................. 554/191 |
| 7,491,522 | B2 | | 2/2009 | Haraldsson | |
| 7,709,668 | B2 | | 5/2010 | Catchpole | |
| 7,828,978 | B2 | * | 11/2010 | Geier et al. | ................... 210/656 |
| 8,481,768 | B2 | | 7/2013 | Sarangan | |

(Continued)

FOREIGN PATENT DOCUMENTS

| CN | 102911795 A | 2/2013 | |
|---|---|---|---|
| EP | 0340635 B1 | 8/1996 | |
| WO | WO 2013/005051 A1 * | 1/2013 | ............. B01D 15/18 |

OTHER PUBLICATIONS

Breivik, H. et al., Preparation of highly purified concentrates of eicosapentaenoic acid and docosahexaenoic acid, 1997 Journal of the american oil chemists' society, vol. 74, No. 11, pp. 1425-1429.*

(Continued)

*Primary Examiner* — Yate K Cutliff
(74) *Attorney, Agent, or Firm* — Richard P. Silverman & Assoc., LLC

(57) ABSTRACT

Disclosed is a process for extracting and purifying EPA (Eicosapentanoic acid) ethyl ester from a crude fish oil feedstock using a combination of novel esterification and simulated moving bed (SMB) techniques. Crude fish oil diluted in non-polar solvent is esterified with an acid and then transesterified with a base. Following washing, the non-polar phase is directly passed to an SMB zone, comprising a normal phase separation with a hydrophilic stationary phase agent and a non-polar/organic polar mobile phase desorbent to provide an enhanced omega-3 product, comprising EPA. In a further embodiment, the enhanced omega-3 product is passed to a second and third SMB zones operating in reverse phase using a hydrophobic stationary phase and a polar mobile phase desorbent. The process is useful for producing high purity EPA at purities in excess of 97 wt-% which are not economically recoverable by conventional distillation methods combined with conventional SMB configurations.

23 Claims, 8 Drawing Sheets

(56) References Cited

U.S. PATENT DOCUMENTS

| | | | |
|---|---|---|---|
| 2007/0181504 A1 | 8/2007 | Binder | |
| 2007/0238886 A1 | 10/2007 | Ho | |
| 2012/0330043 A1* | 12/2012 | Kelliher et al. | 554/193 |
| 2013/0236938 A1* | 9/2013 | Vander Hoff et al. | 435/134 |

OTHER PUBLICATIONS

William W. Christie, "Preparation of Ester Derivatives of Fatty Acids for Chromatographic Analysis", Advances in Lipid Methodology—Two, 1993, pp. 69-111, Oily Press, Dundee, Scotland.

Peter Lembke, "Concentrating Omega-3 Oils-Supercritical Fluid Technology Vers Molecular Distillation", 2011, Brochure titled "Omega-3", available from Bioseuta, USA, at www.bioseutica.com.

Von Schacky, "A Review of Omega-3 Ethyl Esters for Cardiovascular Prevention and Treatment of Increased Blood Triglyceride Levels", Vascu Health Risk Manag., Sep. 2006, 2(3), pp. 251-256, published online by Dove Press.

Arnar Halldorsson, et al., "Separation of EPA and DHA in Fish Oil by Lipase-Catalyzed Esterification With Glycerol", Journ. of American Oil Chemists' Society, 2003, vol. 80, Issue 9, pp. 915-921.

F.V.K. Young, The Chemical & Physical Properties of Crude Fish Oils for Refiners & Hydrogenators, Jun. 1986, Fish Oil Bulletin No. 18, Liverpool, U.K.

Christina Borgese and Marc Privitera, "The Chemistry and Engineering Behind the Boidiesel Process", Biodiesel Magazine, Sep. 8, 2011, pp. 1-3, Published online at http://biodieselmagazine.com/articles/8055/biodiesel-reaction-and-separation-technology.

International Search Report and Written Opinion issued Apr. 22, 2015 in connection with corresponding application PCT/US2015/011638.

* cited by examiner

PROCESS FOR PURIFICATION OF EPA (EICOSAPENTANOIC ACID) ETHYL ESTER FROM FISH OIL

FIELD OF THE INVENTION

The invention relates to a method for extracting and purifying EPA (Eicosapentanoic acid) ethyl ester from a crude fish oil feedstock using a combination of novel esterification and chromatographic techniques. More particularly, the invention provides for separation and purification of EPA ethyl esters from the crude fish oil feedstock using chromatographic technique of simulated moving bed continuous chromatography combined with transesterification. Purified EPA may provide human health benefits. Intake of recommended amounts of DHA and EPA in the form of dietary fish or fish oil supplements may lower triglycerides; reduce the risk of death, heart attack, dangerous abnormal heart rhythms, and strokes in people with known cardiovascular disease; may slows the buildup of atherosclerotic plaques ("hardening of the arteries"); and may slightly lower blood pressure.

BACKGROUND

The principle components of crude fish oil are triglycerides, which represent over 90 percent of the total composition of crude fish oil. The balance consists of partial glycerides, that is mono- or diglycerides, free fatty acids, phospholipids and a group of chemicals known as the unsaponifiable fraction. Crude fish oils are very similar to one another in their physical nature. They are considered as liquid oils; but, in fact, they contain sufficient triglycerides of intermediate melting point for the oils to be partially solid at 20° C.

Fish oil is oil derived from the tissues of oily fish. Fish oils contain the omega-3 fatty acids eicosapentaenoic acid (EPA), and docosahexaenoic acid (DHA) along with other unsaturated triglyceride species including: docosapentanoic acid (DPA), stearadonic acid (SDA), alpha linolenic acid (ALA), gamma linolenic acid (GLA), linoleic acid (LIN) and oleic acid (OLE) and saturated triglycerides including stearic acid (STA) and palmitic acid (PAL). EPA is a poly unsaturated omega-3 fatty acid. In nature the fatty acids combine as triplets with a glycerol back bone forming triglycerides (oil). The structures of EPA and DHA are shown hereinbelow:

matory bowel disease, and other autoimmune diseases such as lupus and rheumatoid arthritis.

The major source of EPA is from marine oils, or fish oil derived from oily fish tissues and are in triglyceride form. Separation of unsaturated fats and fat derivatives from saturated fats and fat derivatives is difficult because the unsaturated components are susceptible to thermal and oxidative degradation and because their physical properties do not differ from those of the saturated components. The concentration of the unsaturated components in the form of parent triglycerides is more difficult, because the fatty acids are randomly arranged on the glycerol backbone of the triglyceride. Therefore the parent oil is usually converted into free fatty acids (FFA) or fatty acid ethyl esters (FAEE) before separation into polyunsaturated and saturated fractions is carried out.

U.S. Pat. No. 7,491,522 to Haraldsson, for example, discloses a process for the lipase-catalyzed esterification of fish oil or marine oil. In Haraldsson, compositions which contain EPA and DHA as free acids or hexyl esters are esterified with ethanol in the presence of a lipase catalyst under essentially organic solvent-free conditions and separated by distillation. The process, the reaction is conducted at 40° C. under vacuum to remove co-produced water. At such conditions, at least a portion of the EPA is lost to isomerization into less valuable components.

The use of urea complexes to separate saturated and monounsaturated fatty acids from polyunsaturated fatty acids has been known since the 1950's. The separation procedure is typically performed by dissolving a mixture of FFA (or fatty acid derivatives) in a hot aqueous alcohol solution that contains the appropriate amount of urea. When the solution is cooled, the urea preferentially forms solid complexes with saturated fatty acids and these are removed by filtration. The aqueous alcohol filtrate solution, which is enriched in unsaturated fatty acids, also contains urea. Therefore the fatty acids are recovered from the filtrate by solvent extraction with a non-polar organic solvent, such as hexane or isooctane, in which the urea is insoluble. U.S. Pat. No. 7,709,668 discloses a process for extracting lipophilic compounds from urea-containing solutions comprising using a near-critical fluid to produce a urea containing precipitate and a near-critical fluid phase containing the lipophilic compound; separating the

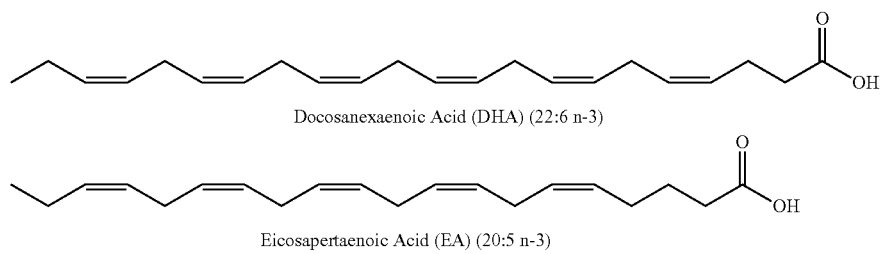

Docosanexaenoic Acid (DHA) (22:6 n-3)

Eicosapertaenoic Acid (EA) (20:5 n-3)

Omega-3 fatty acids are polyunsaturated fatty acids that are essential nutrients for health. Humans need omega-3 fatty acids for numerous normal body functions, such as controlling blood clotting and building cell membranes in the brain, and since human bodies cannot make omega-3 fatty acids, these omega-3 fatty acids must be obtained from food. Omega-3 fatty acids are also associated with many human health benefits, including protection against heart disease and possibly stroke. Recent studies are identifying potential benefits for a wide range of conditions including cancer, inflamnear-critical fluid phase from the urea containing precipitate; and reducing the pressure of the near-critical fluid phase to recover the lipophilic compound.

Heating fatty acids either in the transesterification of triglycerides to fatty acid esters, or in the subsequent separation of the desired fatty acid derivative from a solvent or co-solvent has been shown to isomerize the EPA molecules and reduce the overall recovery of these valuable components.

Previous methods for extraction of EPA, DHA and other useful polyunsaturated fatty acids from their triglycerides, have not been satisfactory for the purification of fatty acids from crude fish oils, or for the production of highly pure fatty acids. The term "purity" is used here to mean not only in the sense of being separated from all other fatty acids of different chain lengths and different number and placement of unsaturations, but also purity of the particular cis-trans structure. Prior art methods not only did not yield sufficient purity, but in many cases also required such extreme physical and chemical conditions as to cause some degree of degradation of the fatty acids, formation of peroxides, and/or conversion of at least some of the cis-bonds to the less desirable trans form.

All of the existing efforts in purifying EPA Ethyl Esters have revolved around chemical reconstitution, enzymatic treatment or crystallization. With the introduction of Simulated Moving Bed applications achieving a maximum EPA purity of 97% is possible at higher throughput and recovery.

It is an objective of the present invention to provide a process for the recovery and purification of EPA from crude fish oils and for the production of a high purity EPA product.

SUMMARY

The process of the present invention relates to the purification of EPA (Eicosapentanoic acid) ethyl ester from a fish oil feedstock using novel esterification in combination with chromatographic techniques. More specifically, Applicant has developed a novel combination process to convert the triglycerides found in crude fish oils to ethyl esters in a transesterification zone at a low temperature and separate the transesterification reaction product with a Simulated Moving Bed (SMB) system to bring about the separation and purification of EPA Ethyl Ester from the entire range of ethyl esters formed in the transesterification reaction zone. The use of a hydrocarbon solvent in the transesterification zone permits the product of the transesterification reaction to be passed directly to the SMB zone, without an intermediate evaporation step, because the same solvent is comprised in the desorbent in the SMB zone. The simulated moving bed system employed is a normal phase SMB using a silica based stationary phase adsorbent in combination with a non-polar desorbent to both separate and purify the transesterified fish oils to provide an enriched extract stream rich in EPA, a primary raffinate stream comprising a mixture of other alkyl esters, and a secondary raffinate stream which can be used directly to offset the mobile phase desorbent stream in the SMB zone. The primary raffinate can be evaporated to recover mobile phase desorbent from oil phase which can be used as a biodiesel product. An EPA product having a purity greater than 97 wt percent (e.g., 98, 99, 99.5 wt-%) following solvent removal can be obtained.

In one embodiment, the invention is a process for recovering an enhanced omega-3 ester product from a crude fish oil comprising fatty acids of omega-3 fatty acids of eicosapentaenoic acid (EPA) or docosahexaenoic acid (DHA) along with other unsaturated triglyceride species including at least one of docosapentanoic acid (DPA), stearadonic acid (SDA), alpha linolenic acid (ALA), gamma linolenic acid (GLA), linoleic acid (LIN) and oleic acid (OLE) and free fatty acids. The process comprises:

a. passing the crude fish oil to a solvent mixing zone and therein admixing the crude fish oil with a non-polar solvent to provide a fish oil/solvent mixture;

b. passing the fish oil/solvent mixture to an esterification zone and therein subjecting the fish oil/solvent mixture to an esterification reaction in the presence of an ethanol stream and an acid catalyst stream comprising a mineral acid at effective esterification conditions to convert the free fatty acids to Fatty Acid Ethyl Esters (FAEE) to provide a non-polar esterification reaction effluent stream comprising non-polar solvent, fatty acids of omega-3 fatty acids of EPA or DHA or mixtures of EPA and DHA, and the unsaturated triglyceride species, and a polar esterification reaction phase comprising ethanol, water, the FAEE, and the mineral acid;

c. admixing the non-polar esterification reaction effluent stream with a polar solvent stream to form a transesterification reaction feed stream and passing the transesterification feed stream to a transesterification zone and subjecting the transesterification feed stream to a transesterification reaction in the presence of a basic catalyst stream at effective transesterification reaction conditions to convert the fatty acids of omega-3 fatty acids of EPA or DHA to omega-3 fatty acid esters comprising EPA or DHA or mixtures of EPA and DHA, and to convert the unsaturated triglycerides to glycerol and to other fatty acid ethyl esters of LIN, OLE and at least one of DPA, SDA, ALA, and GLA to provide a two-phase transesterification reaction effluent stream;

d. passing the two-phase transesterification reaction effluent stream to a wash/separation zone and therein washing the two-phase transesterification reaction effluent stream with water, stabilizing, and phase separating the two-phase transesterification reaction effluent stream to provide an aqueous phase stream comprising the polar solvent, water and glycerol, and a non-polar transesterification effluent stream comprising water, non-polar solvent, omega-3 fatty acid esters and the other fatty acid esters of LIN, OLE and at least one of DPA, SDA, ALA, and GLA;

e. finishing the non-polar transesterification effluent stream to remove water in a finishing zone to provide a finished feed stream comprising non-polar solvent, omega-3 fatty acid esters and other fatty acid esters;

f. passing the finished feed stream and a mobile phase desorbent to a normal phase simulated moving bed adsorption (SMB) zone, the normal phase SMB zone containing a hydrophilic stationary phase agent, the normal phase SMB zone comprising a plurality of adsorbent beds and operating in an effective normal phase cycle, the mobile phase desorbent comprising a non-polar solvent and an organic polar solvent in an effective normal phase solvent ratio to provide an SMB extract stream, a primary SMB raffinate stream, and a secondary SMB raffinate stream a portion of which is recycled to provide at least a portion of the mobile phase desorbent, the SMB extract stream comprising non-polar solvent and omega-3 fatty acid esters and other fatty acid esters of at least one of DPA, SDA, ALA, and GLA and being essentially free of OLE and LIN, the primary SMB raffinate stream comprising non-polar solvent and fatty acid esters of OLE and LIN;

g. passing the first SMB extract stream to a first extract solvent recovery zone and therein recovering the non-polar solvent to provide the enhanced omega-3 ester product comprising EPA or DHA or mixtures thereof and a first SMB recovered solvent stream comprising the non-polar solvent, and passing the primary raffinate stream to a raffinate solvent recovery zone and therein recovering the non-polar solvent to provide an SMB reject stream and a second SMB recovered solvent stream comprising the non-polar solvent and the polar organic solvent; and, h. returning at least a portion of the first SMB recovered solvent stream and the second recovered solvent stream to be admixed with the mobile phase desorbent.

In a further embodiment, the invention is a process for preparing a high purity EPA product from a crude fish oil comprising a crude fish oil comprising fatty acids of omega-3 fatty acids of eicosapentaenoic acid (EPA) or docosahexaenoic acid (DHA) along with other unsaturated triglyceride species including at least one of docosapentanoic acid (DPA), stearadonic acid (SDA), alpha linolenic acid (ALA), gamma linolenic acid (GLA), linoleic acid (LIN) and oleic acid (OLE) and free fatty acids. The process comprises:

a. passing the crude fish oil to a solvent mixing zone and therein admixing the crude fish oil with a non-polar solvent to provide a fish oil/solvent mixture;

b. passing the fish oil/solvent mixture to an esterification zone and therein subjecting the fish oil/solvent mixture to an esterification reaction in the presence of an ethanol stream and an acid catalyst stream comprising a mineral acid at effective esterification conditions to convert the free fatty acids to Fatty Acid Ethyl Esters (FAEE) to provide a non-polar esterification reaction effluent stream comprising non-polar solvent, fatty acids of omega-3 fatty acids of EPA or DHA or mixtures of EPA and DHA, and the unsaturated triglyceride species, and a polar esterification reaction phase comprising ethanol, water, the FAEE, and the mineral acid;

c. admixing the non-polar esterification reaction effluent stream with a polar solvent stream to form a transesterification reaction feed stream and passing the transesterification feed stream to a transesterification zone and subjecting the transesterification feed stream to a transesterification reaction in the presence of a basic catalyst stream at effective transesterification reaction conditions to convert the fatty acids of omega-3 fatty acids of EPA or DHA to omega-3 fatty acid esters comprising EPA or DHA or mixtures of EPA and DHA, and to convert the unsaturated triglycerides to glycerol and to other fatty acid ethyl esters of LIN, OLE and at least one of DPA, SDA, ALA, and GLA to provide a two-phase transesterification reaction effluent stream;

d. passing the two-phase transesterification reaction effluent stream to a wash/separation zone and therein washing the two-phase transesterification reaction effluent stream with water, stabilizing, and phase separating the two-phase transesterification reaction effluent stream to provide an aqueous phase stream comprising the polar solvent, water and glycerol, and a non-polar transesterification effluent stream comprising water, non-polar solvent, omega-3 fatty acid esters and the other fatty acid esters of LIN, OLE and at least one of DPA, SDA, ALA, and GLA;

e. finishing the non-polar transesterification effluent stream to remove water in a finishing zone to provide a finished feed stream comprising non-polar solvent, omega-3 fatty acid esters and other fatty acid esters;

f. passing the filtered feed stream and a first stage mobile phase desorbent to a normal phase simulated moving bed adsorption (SMB) zone, the normal phase SMB zone containing a hydrophilic stationary phase agent, the normal phase SMB zone comprising a plurality of adsorbent beds and operating in an effective normal phase cycle, the first stage mobile phase desorbent comprising a non-polar solvent and an organic polar solvent in an effective first stage solvent ratio to provide a first SMB extract stream, a first primary SMB raffinate stream, and a first secondary SMB raffinate stream which is recycled to provide at least a portion of the first stage mobile phase desorbent, the first SMB extract stream comprising non-polar solvent and omega-3 fatty acid esters and other fatty acid esters of at least one DPA, SDA, ALA, and GLA and being essentially free of OLE and LIN, the first primary SMB raffinate stream comprising non-polar solvent and fatty acid esters of OLE and LIN;

g. passing the first SMB extract stream to a first extract solvent recovery zone and therein recovering the non-polar solvent to provide a first extract stream and a first SMB1 recovered solvent stream comprising the non-polar solvent, and passing the first primary raffinate stream to a first raffinate solvent recovery zone and therein recovering the non-polar solvent to provide a first SMB reject stream and a second SMB recovered solvent stream comprising the non-polar solvent the first extract solvent and admixing at least a portion of the first and second SMB recovered solvent stream with the first stage mobile phase desorbent;

h. diluting the first extract stream with an effective amount of a polar solvent and counter-currently passing the diluted first extract stream and a second stage mobile phase desorbent to a first reverse phase simulated moving bed adsorption (SMB) zone, the first reverse phase SMB zone containing hydrophobic stationary phase agent, the first reverse phase SMB zone comprising a plurality of adsorbent beds and operating in an effective reverse phase cycle, the second stage mobile phase desorbent comprising a polar solvent and water in an effective second stage solvent ratio to provide a second SMB extract stream, a second primary SMB raffinate stream, and a second secondary SMB raffinate stream which is recycled to provide at least a portion of the second stage mobile phase desorbent, the second primary SMB raffinate stream comprising polar solvent and fatty acid esters of EPA, the second primary SMB raffinate stream comprising polar solvent and fatty acid ester of DHA, and other fatty acid esters of at least one DPA, SDA, ALA, and GLA;

i. passing the second primary SMB raffinate stream to a second extract solvent recovery zone and therein recovering the polar solvent to provide a second raffinate stream and a first SMB2 recovered solvent stream comprising the polar solvent, and passing the second extract stream to a second extract solvent recovery zone and therein recovering the polar solvent to provide a second SMB reject stream and a second SMB2 recovered solvent stream comprising the non-polar solvent the first extract solvent;

j. diluting the second raffinate stream with an effective amount of the polar solvent and counter-currently passing the diluted second raffinate stream and a third stage mobile phase desorbent to a second reverse phase simulated moving bed adsorption (SMB) zone, the third reverse phase SMB zone containing hydrophobic stationary phase agent, the third reverse phase SMB zone comprising a plurality of adsorbent beds and operating in an effective reverse phase cycle, the third stage mobile phase desorbent comprising a polar solvent and water in an effective third stage solvent ratio to provide a third SMB extract stream, a third primary SMB raffinate stream, and a third secondary SMB raffinate stream which is recycled to provide at least a portion of the third stage mobile phase desorbent, the third primary SMB raffinate stream comprising polar solvent and fatty acid esters of DHA and other fatty acid esters of at least one DPA, SDA, ALA, and GLA, the third SMB extract stream comprising polar solvent and fatty acid ester of EPA; and, k. passing the third primary SMB raffinate stream to a third raffinate solvent recovery zone and therein recovering the polar solvent to provide a third SMB reject stream and a first SMB3 recovered solvent stream comprising the polar solvent, and passing the third extract stream to a third extract solvent recovery zone and therein recovering the polar solvent to provide a high purity EPA product stream and a second SMB3 recovered solvent stream comprising the polar solvent the first extract solvent.

DETAILED DESCRIPTION OF THE INVENTION

Figure 1:
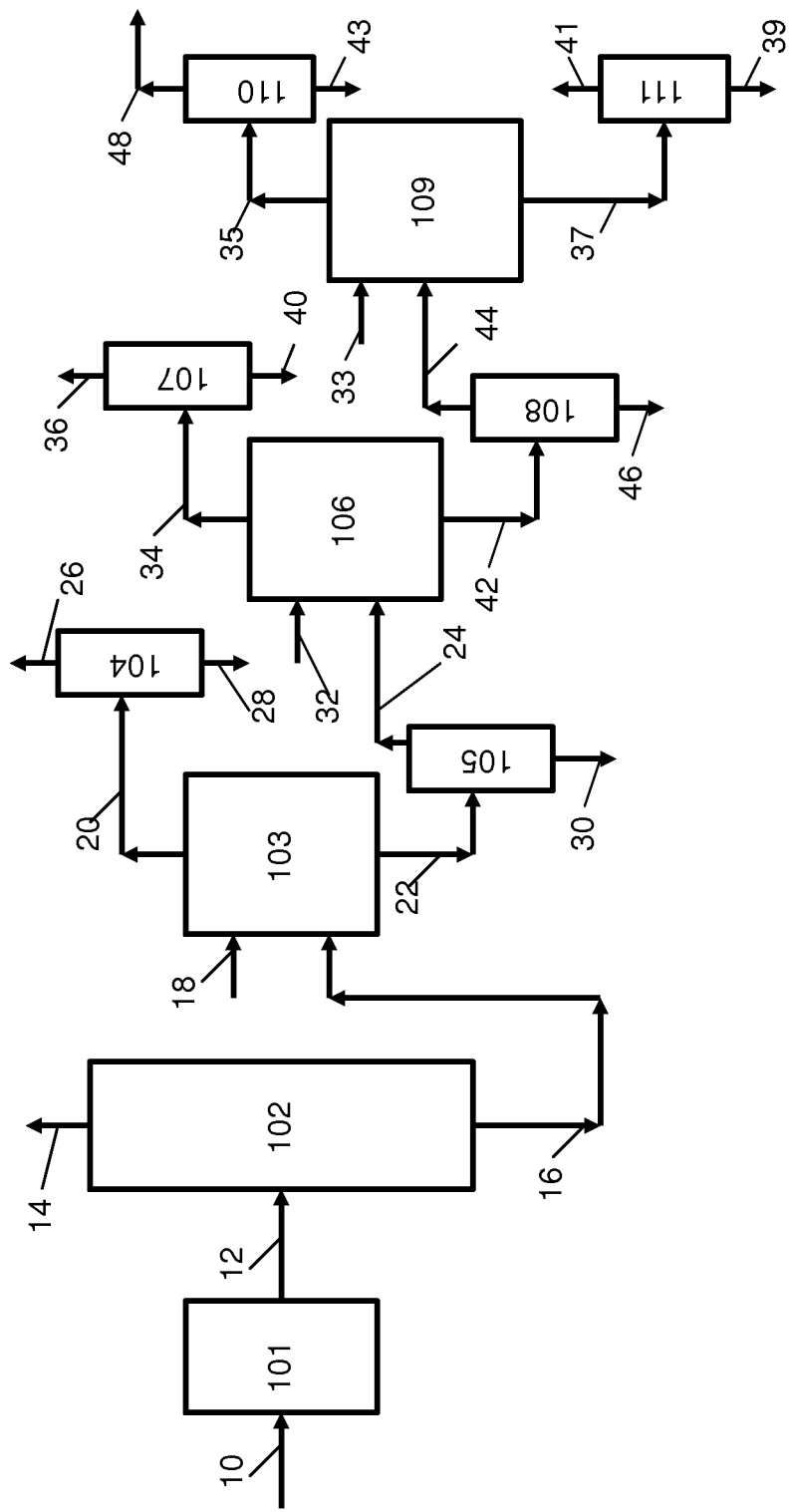
FIG. 1 is a schematic process flow diagram illustrating the prior art.

Crude fish oil as described hereinabove comprises a number of fatty acid components. In the present invention, these fatty acid components are first converted to ester form, prior to separation. The major fatty acid ester components are listed in Table 1 and will be referred to by the abbreviation shown in Table 1 for each of the corresponding major component.

TABLE 1

Nomenclature and Abbreviations for Fatty Acids

| Component | Abbreviation | NAME OF COMPONENT |
|---|---|---|
| C18:1 | OLE | OLEIC ACID |
| C18:2 | LIN | LINOLEIC ACID |
| C18:3 | ALA | ALPHA LINOLENIC ACID |
| C18:4 | SDA | STEARADONIC ACID |
| C20:4 | ETA | EICOSATETRAENOIC ACID |
| C20:5 | EPA | EICOSAPENTAENOIC ACID |
| C22:5 | DPA | DOCOSAPENTANOIC ACID |
| C22:6 | DHA | DOCOSAHEXAENOIC ACID |

The first number in the first column of Table 1, indicates the length of the carbon chain in the fatty acid ester molecule, and the second number indicates the number of double bonds in the molecule. Undesirable isomers of EPA created by heat degradation in separation process are generally referred to as ISO-A, ISO-B, ISO-C, ISO-D and ISO-E. The components: OLE and LIN were found to be major impurities which can interfere with the production of high purity EPA. It was surprisingly discovered that the OLE and LIN interfere with the reverse phase SMB operation by requiring additional desorbent to regenerate the adsorbent beds and because the presence of OLE and LIN reduces the overall capacity of the SMB zone to produce the high purity EPA product.

Typically, crude fish oil is esterified at conventional esterification temperatures above about 60° C. The resulting conventionally esterified effluent is water washed and passed to a molecular distillation process for the separation of lower carbon number esters and to enrich the concentration of the Omega-3 ester components. The molecular distillation is typically carried out at a molecular distillation temperature in excess of about 200° C. at very low pressures of about 1 to about 10 mBar. This heating during the molecular distillation results in the breakdown of the EPA and causes isomers of EPA to form. The lower carbon number fatty acid esters and the isomers of EPA act as impurities in the subsequent purification steps to obtain a high purity EPA product.

In a conventional EPA purification process, the conventional esterification step is followed by the molecular distillation step and the resulting enriched EPA stream can passed to a cascade comprising 2 or more simulated moving bed SMB zones operating as reverse phase SMB's which use a hydrophobic stationary phase and a polar mobile phase desorbent. Unfortunately, the low carbon number fatty acid esters, such as OLE and LIN act as impurities and limit the purity of the final high purity EPA product to about 97 wt-% or less, and also reduce the recovery of the valuable high purity EPA product.

Applicant surprisingly discovered that by employing a two-step esterification process comprising firstly contacting the crude fish oil in a pre-transesterification step with a mineral acid catalyst dispersed in a non-polar medium, and secondly passing the pre-transesterification effluent to an esterification zone wherein the pre-transesterification is contacted with a basic catalyst in a non-polar medium combined with a normal phase SMB zone, significantly improves the recovery and purity of the high purity EPA product. Applicant found that the esterification zone having an effective esterification temperature less than 40° C., and more preferably less than about 30° C. significantly reduces the losses of EPA by reducing the production of EPA isomers A-E. It is believed that these advantages are achieved in the esterification steps because conducting the esterification steps with an effective amount of alcohol, such as ethanol in water in both the pre-transesterification zone and in the esterification zone of the instant invention, the reactions take place in a two-phase reaction zone wherein the esterification reaction takes place at the non-polar/polar solvent interface. Because the ester form of the fatty acids in the fish oil are not soluble in the polar solvent phase, they are immediately removed from the reaction zone at the interface between the polar and non-polar phases and migrate to and become concentrated in the non-polar phase as the reaction proceeds. This results in fewer impurities in the resulting esterified effluent streams because the two-phase esterification reactions are carried out at low temperatures, i.e., essentially ambient conditions, thereby creating fewer isomer impurities. In the present invention, essentially no EPA isomers, such as ISO-A, ISO-B, ISO-C, and ISO-D and ISO-E are formed. Following the esterification steps, the esterified effluent is passed to a novel normal phase SMB zone employing a hydrophilic adsorbent, such as silica, and a non-polar mobile phase desorbent such as hexane:ethyl acetate, to provide an enriched EPA stream, which after solvent separation comprises few impurities such as OLE or LIN. The elimination of the OLE, LIN, and EPA isomers permit the production of a high purity EPA product having an EPA purity of greater than 97 wt-%, preferably greater than 98 wt-%, and more preferably a high purity EPA product having an EPA purity greater than 99 wt-%.

Stationary Phase

The stationary phase adsorbent for use in the normal phase SMB zone is a hydrophilic adsorbent, such as silica. It was found that silica provided higher selectivities for separating Omega-3 components than hydrophobic adsorbents such as coated silica adsorbents such as C8 or C18. Batch chromatographic separation showed the ability of the silica adsorbent to perform the enrichment of the EPA component while significantly reducing the concentration of the OLE and LIN components in the extract stream by using a non-polar solvent as the loading solvent and a polar solvent as the desorbent solvent. Preferably the stationary phase adsorbent is silica having a particle diameter of between about 300 and about 500 microns.

Mobile Phase Desorbent

The mobile phase desorbent of the present invention for use in the normal phase SMB zone is a mixture of a non-polar solvent such as n-heptane or hexane, and a polar organic solvent such as ethyl acetate. Preferably, the selective mobile phase desorbent comprises from 95 to 99 parts non-polar solvent such as n-heptane or hexane to 5-1 parts polar organic compound, such as ethyl acetate, and most preferably, the selective mobile phase desorbent comprises a ratio of 98 parts n-heptane or hexane to 2 parts ethyl acetate.

Transesterification

In the present invention, the crude fish oil is admixed with a non-polar solvent to form a fish oil/non-polar solvent mixture. Preferably, the fish oil/solvent mixture comprises a ratio of non-polar solvent to fish oil of from about 2 to about 3 times the volume of the fish oil. More preferably, the fish oil/solvent mixture comprises a ratio of non-polar solvent to fish oil of from about 2.3 to about 2.7 times the volume of the fish oil. Most preferably, the fish oil/solvent mixture comprises a ratio of non-polar solvent to fish oil of from about 2.5 times the volume of the fish oil. Typically, crude fish oil will contain from about 1 to about 5 wt-% Free Fatty Acids FFA. If these FFA's are permitted to remain in the fish oil/solvent mixture in the transesterification step, they will be converted to soaps. To avoid the formation of soaps, the FFA's are first converted to ethyl esters in a pre-transesterification step, or esterification step. In the esterification step, the fish oil/solvent mixture is admixed with a polar solvent such as ethanol or ethanol in water in to form an esterification reaction mixture and the esterification reaction mixture is contacted with a mineral acid catalyst. Preferably, the acid catalyst stream comprises a 0.1 Normal sulfuric acid solution. The acid catalyst stream is admixed with the esterification reaction mixture with an effective amount of the acid catalyst stream to the convert essentially all of the free fatty acids with ethanol to form fatty acid ethyl esters. The esterification reaction takes place at effective esterification conditions including an esterification reaction temperature at or below room temperature (25° C.). At the conclusion of the esterification reaction, the non-polar and polar phases are allowed to form and a non-polar esterification reaction effluent comprising solvent, fish oil and ethyl esters is withdrawn, and a polar esterification effluent comprising ethanol, water and sulfuric acid is withdrawn. The non-polar esterification reaction effluent is passed to a transesterification zone, and therein admixed with a polar solvent stream to form a transesterification reaction mixture and the transesterification reaction mixture is contacted with a basic catalyst stream. The polar solvent stream is selected from the group consisting of methanol, ethanol and isopropanol. Preferably, the polar solvent comprises ethanol. The basic catalyst stream comprises a base metal hydroxide such a sodium or potassium hydroxide and dissolved in ethanol. Thus, the transesterification reaction is a two-phase reaction zone wherein the esterification reaction takes place at the non-polar/polar solvent interface. Because the ester form of the fatty acids in the fish oil are not soluble in the polar solvent phase, they are immediately removed from the reaction zone at the interface between the polar and non-polar phases and migrate to and become concentrated in the non-polar phase as the reaction proceeds. During the reaction, the transesterification reaction zone is maintained at effective transesterification reaction conditions including a reaction temperature at or below room temperature and the reaction mixture is continuously stirred. By maintaining the transesterification temperature at or below room temperature (25° C.), any side reactions which could potentially destroy valuable EPA or DHA are thus minimized. Glycerol is produced as a byproduct of the transesterification reaction and remains in the polar phase without requiring separate distillation steps. The removal of the ester form into the non-polar phase further serves to improve conversion by separating the ester phase from any water formed in the reaction which if contacted with the ester could reverse the reaction.

DETAILED DESCRIPTION OF THE DRAWINGS

Prior Art Scheme

FIG. 1 illustrates a prior art scheme for purifying a crude fish oil stream to recover an enriched EPA product stream using multiple simulated moving bed separation zones and conventional esterification techniques of the prior art. According to FIG. 1 (Prior Art), the crude fish oil stream in line 10 is passed to a conventional esterification zone 101, wherein the crude fish oil is subjected to, for example, esterification with ethanol in the presence of a lipase catalyst under essentially organic solvent-free conditions as disclosed in U.S. Pat. No. 7,491,522 to provide an esterification effluent stream in line 12. The resulting esterification effluent in line 12 is passed to a distillation zone 102 wherein the esterification is separated by molecular distillation in the conventional manner to provide a first reject stream in line 14 and an omega-3 fish oil concentrate in line 16. The omega-3 fish oil concentrate in line 16 is passed to a cascade of three SMB zones to purify and recover a product stream having an EPA purity of 97 wt-% EPA on a solvent free basis, or less. Accordingly, the omega-3 fish oil concentrate in line 16 as a first SMB feed stream in line 16 and a first desorbent stream in line 18 comprising a mixture of methanol and water are passed to a first SMB (simulated moving bed) zone 103. Typically, the desorbent stream has a ratio of methanol to water of about 98:2 on a volume basis. The first SMB zone 103 has a plurality of adsorbent beds containing a stationary phase adsorbent and arranged serially in a manner which is described hereinbelow in FIG. 3. The stationary phase desorbent is a hydrophobic C18 adsorbent. A first SMB extract stream in line 20 is withdrawn from the first SMB zone and passed to a first extract solvent recovery zone 104 to provide a second reject stream in line 26 and a first SMB1 recovered solvent stream in line 28. A first stage raffinate stream is withdrawn in line 22 and passed to a first raffinate solvent recovery zone 105 to provide a first evaporated raffinate stream in line 24 and a second SMB1 recovered solvent stream in line 30. At least a portion of each of the first SMB1 recovered solvent stream in line 28 and the second SMB1 recovered solvent stream in line 30 are recycled to makeup a portion of the desorbent stream in line 18. The first evaporated raffinate stream in line 24 as a second feed stream in line 24 and a second desorbent stream in line 32 comprising a mixture of methanol and water are passed to a second stage of SMB separation (SMB2) 106. Typically, the second desorbent stream has a ratio of methanol to water of about 93:7 on a volume basis. The second SMB zone 106 has a plurality of adsorbent beds containing a stationary phase adsorbent and arranged serially in a manner which is described hereinbelow in FIG. 3. The stationary phase desorbent is a hydrophobic C18 adsorbent. A second SMB extract stream in line 34 is withdrawn from the first SMB zone and passed to an SMB2 extract solvent recovery zone 107 to provide an SMB2 reject stream in line 36 and a first SMB2 recovered solvent stream in line 40. A second raffinate stream is withdrawn from the second SMB zone in line 42 and passed to an SMB2 raffinate solvent recovery zone 108 to provide a second evaporated raffinate stream in line 44 and a second SMB2 recovered solvent stream in line 46. At least a portion of each of the first SMB2 recovered solvent stream in line 40 and the second SMB2 recovered solvent stream in line 46 are recycled to makeup a portion of the desorbent stream in line 32. The second evaporated raffinate stream in line 44 and a third desorbent stream in line 32 comprising a mixture of methanol and water are passed to a third SMB zone (SMB3) 109. Typically, the third desorbent stream has a ratio of methanol to water of about 93:7 on a volume basis. The third SMB zone 109 has a plurality of adsorbent beds containing a stationary phase adsorbent and arranged serially in a manner which is described hereinbelow in FIG. 3. The stationary phase adsorbent in the third SMB zone 109 is a hydrophobic C18 adsorbent. A third SMB extract stream in line 35 is withdrawn from the third SMB zone 109 and passed to an SMB3 extract solvent recovery zone 110 to provide high purity EPA product stream in line 48 and a first SMB3 recovered solvent stream in line 43. A third raffinate stream is withdrawn from the third SMB zone in line 37 and passed to an SMB3 raffinate solvent recovery zone 111 to provide a third evaporated raffinate stream in line 41 and a second SMB3 recovered solvent stream in line 46. At least a portion of each of the first SMB3 recovered solvent stream in line 43 and the second SMB3 recovered solvent stream in line 39 are recycled to makeup a portion of the desorbent stream in line 33. At least a portion of the first and second reject streams (14 and 26) and the SMB2 reject stream (36) and a third evaporated raffinate stream in line 41 are recovered as components of biodiesel or passed to disposal. The high purity EPA product stream in line 48 comprises an EPA concentration of about 97 wt-% on a solvent free basis. The operation of the first, second, and third SMB zones are disclosed in US Publication No. 2012/0330043.

Inventive Scheme

Figure 2:
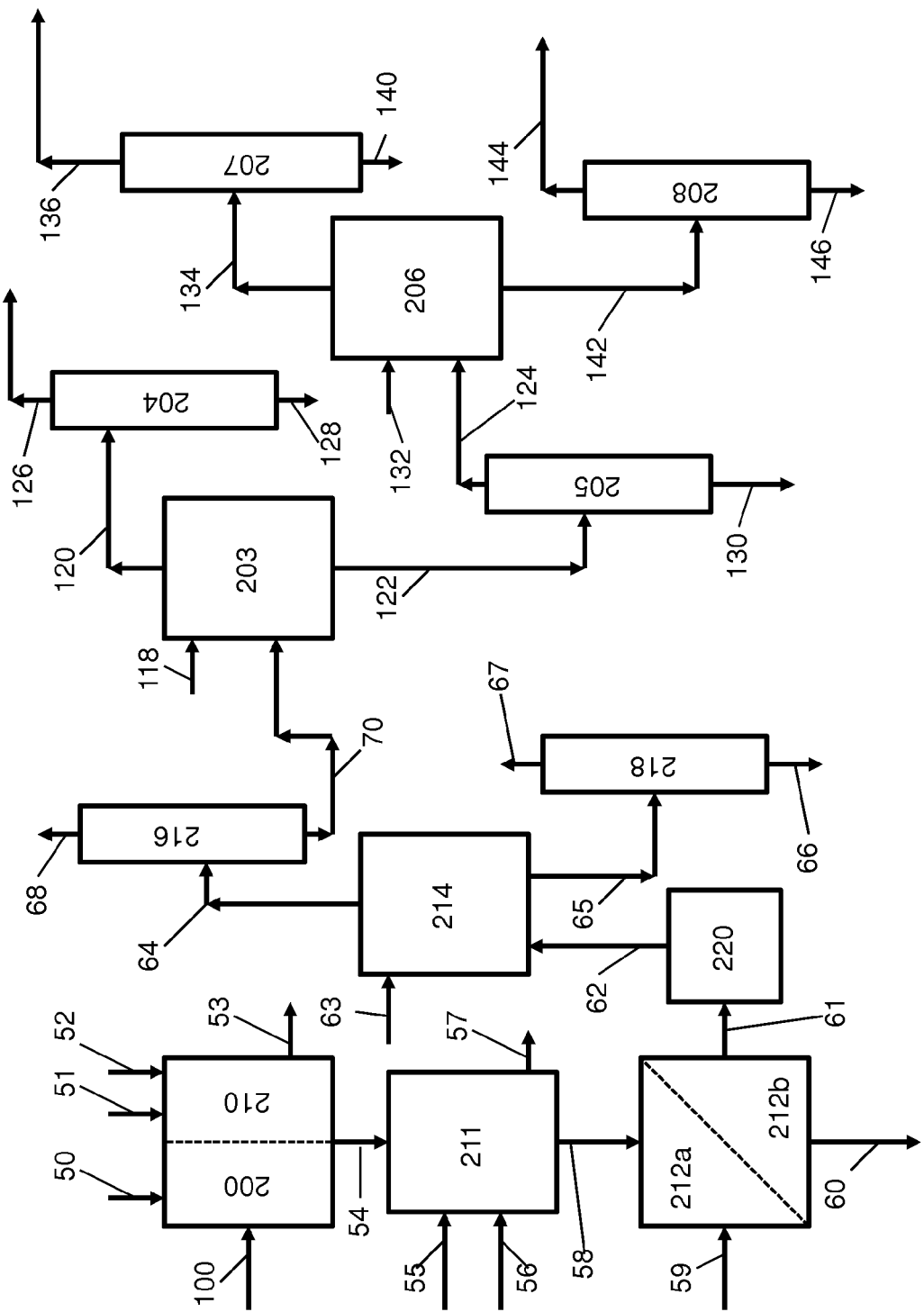
FIG. 2 is a schematic process flow diagram illustrating one embodiment of the invention.

According to one embodiment of the invention and with reference to FIG. 2, a crude fish oil stream in line 100 is passed to a solvent mixing zone 200, wherein the crude fish oil stream in line 100 is admixed with a non-polar solvent stream in line 50 to provide a fish oil/solvent mixture. The crude fish oil stream comprises fatty acids of omega-3 fatty acids of eicosapentaenoic acid (EPA) or docosahexaenoic acid (DHA) along with other unsaturated triglyceride species including at least one of docosapentanoic acid (DPA), stearadonic acid (SDA), alpha linolenic acid (ALA), gamma linolenic acid (GLA), linoleic acid (LIN) and oleic acid (OLE) and free fatty acids, and depending upon the source also may contain saturated triglycerides including stearic acid (STA) and palmitic acid (PAL). Preferably, the non-polar solvent is selected from the group consisting paraffinic hydrocarbons such as hexane and heptane. More preferably, the non-polar solvent is heptane. Preferably, the fish oil/solvent mixture comprises a ratio of non-polar solvent to fish oil of from about 2 to about 3 times the volume of the fish oil. More preferably, the fish oil/solvent mixture comprises a ratio of non-polar solvent to fish oil of from about 2.3 to about 2.7 times the volume of the fish oil. Most preferably, the fish oil/solvent mixture comprises a ratio of non-polar solvent to fish oil of from about 2.5 times the volume of the fish oil. When the crude fish oil/solvent mixture is subjected an esterification reaction in the presence of a base and ethanol is introduced, the triglycerides are converted to esters and any free fatty acids are converted to Fatty Acid Ethyl Esters FAEE by acid catalyzed esterification process. Typically, the crude fish oil contains from about 1 to about 5 wt-% Free Fatty Acids FFA. If these FFA's are permitted to remain in the fish oil/solvent mixture in the transesterification step, they will be converted to soaps. To avoid the formation of soaps, the FFA's are first converted to ethyl esters in a pre-transesterification step, or esterification step in an esterification zone 210. In the esterification zone 210, the fish oil/solvent mixture is admixed with a polar solvent such as ethanol or ethanol in water in line 52 to form an esterification reaction mixture and the esterification reaction mixture is contacted with an acid catalyst stream comprising a mineral acid in line 51. Preferably, the acid catalyst stream comprises a 0.1 Normal sulfuric acid solution. The acid catalyst stream in line 51 is admixed with the esterification reaction mixture with an effective amount of the acid catalyst stream to the convert essentially all of the free fatty acids with ethanol to form fatty acid ethyl esters, wherein the effective amount of acid catalyst is at least about 5 wt-% of the weight of the crude fish oil in the esterification reaction mixture. The esterification reaction takes place at effective esterification conditions including an esterification reaction temperature at or below room temperature of 25° C. At the conclusion of the esterification reaction, water is introduced and the non-polar and polar phases are allowed to form. Non-polar esterification reaction effluent comprising solvent, fish oil and ethyl esters are withdrawn in line 54, and a polar esterification effluent comprising ethanol, water and sulfuric acid is withdrawn in line 53. The non-polar esterification reaction effluent in line 54 is passed to a transesterification zone 211, and therein admixed with a polar solvent stream in line 56 to form a transesterification reaction mixture and the transesterification reaction mixture is contacted with an effective amount of a basic catalyst stream in line 55. The polar solvent stream is selected from the group consisting of methanol, ethanol and isopropanol. Preferably, the polar solvent comprises ethanol. The basic catalyst stream in line 55 comprises a base metal hydroxide such a sodium or potassium hydroxide and dissolved in ethanol. The effective amount of the base metal hydroxide in the transesterification reaction zone is about 2 wt-% of the weight of the crude fish oil. Thus, the transesterification reaction zone 211 is a two-phase reaction zone wherein the esterification reaction takes place at the non-polar/polar solvent interface. Because the ester form of the fatty acids in the fish oil are not soluble in the polar solvent phase, they are immediately removed from the reaction zone at the interface between the polar and non-polar phases and migrate to and become concentrated in the non-polar phase as the reaction proceeds. During the reaction, the transesterification reaction zone is maintained at effective transesterification reaction conditions including a reaction temperature at or below room temperature (25° C.) and the reaction mixture is continuously stirred. By maintaining the transesterification temperature at or below a room temperature of 25° C., any side reactions which could potentially destroy valuable EPA or DHA are minimized. Glycerol is produced as a byproduct of the transesterification reaction. The removal of the ester form into the non-polar phase further serves to improve conversion by separating the ester phase from any water formed in the reaction which if contacted with the ester could reverse the reaction. The two-phase transesterification reaction effluent stream in line 58 is withdrawn from the transesterification zone 211 and passed to a wash/separation zone 212a/212b. In the wash/separation zone 212a/212b, the two-phase transesterification reaction effluent stream in line 58 is washed with water introduced via line 59; and, after stabilization and subsequent phase separation provides an aqueous phase in line 60 comprising ethanol, water and glycerol, and a non-polar transesterification effluent stream in line 61. The non-polar transesterification effluent stream in line 61 comprises the non-polar solvent, triglycerides, water, alcohol such as methanol, and ethyl esters. The non-polar transesterification effluent stream in line 61 is passed directly to a finishing zone, or finishing column 220 containing an adsorbent such as silica to remove any remaining water and alcohol from the transesterification effluent in line 61 to provide a finished feed stream in line 62, which is essentially free of water and alcohol. By essentially free of water and alcohol, it is meant that the amount of water and alcohol in the finished stream is less than 100 ppm. The finished feed stream in line 62 is passed to a cascade of three SMB zones to obtain a high purity EPA product stream; however, this cascade differs from the cascade shown in FIG. 1 in that the first SMB zone 214 is a normal phase SMB using a hydrophilic stationary phase agent and using a first stage mobile phase desorbent comprising a non-polar solvent/organic polar solvent mixture in an effective ratio of non-polar solvent to organic polar solvent. It was surprisingly discovered that essentially all of the OLE and LIN major impurities can be removed from the extract of the first SMB zone of the present invention. The prior art scheme is not able to completely remove OLE and LIN. Any remaining traces of OLE and LIN remain in the final EPA product, thus reducing the purity of the final EPA product. The second SMB zone 203 and the third SMB zone 206 employ a reversed phase SMB mode using a hydrophobic stationary phase agent and a second and third stage mobile phase desorbent comprising a polar solvent. Referring again to FIG. 2, the finished feed stream in line 62 and a first SMB desorbent stream in line 63 are passed to the first SMB zone to provide a first SMB extract stream in line 64 and a first primary SMB raffinate stream in line 65. The first primary SMB raffinate stream in line 65 comprises the non-polar solvent, and non-Omega-3 ethyl esters such as OLE (Oleic), LIN (Linoleic), and optionally, palmetic. A first secondary SMB raffinate stream, not shown, is also produced and employed directly as first mobile phase desorbent recycle stream of which at least a portion is combined with the first mobile phase desorbent stream in line 63 to offset the overall requirement for the first mobile phase desorbent stream. The first mobile phase desorbent stream in line 63 comprises a mixture of from 95 to 99 parts n-heptane or hexane to 5-1 parts a polar organic compound, such as ethyl acetate. Most preferably, the first mobile phase desorbent stream comprises a ratio of 98:2 parts n-heptane to ethyl acetate. The first SMB zone 214 has a plurality of adsorbent beds (at least 8) containing a stationary phase adsorbent and arranged serially in a manner which is described hereinbelow in FIG. 3. The first stationary phase adsorbent is a silica adsorbent. The first SMB extract stream in line 64 comprises heptane, ethyl acetate, omega-3 fatty acid esters and other fatty acid esters of at least one of DPA, SDA, ALA, and GLA. The first SMB extract stream in line 64 is essentially free of any OLE or LIN; that is, that there was no detectable concentration of OLE or LIN in the first SMB extract stream. More particularly, by essentially free of OLE or LIN, there is less than 0.1 wt-% of either LIN or OLE in the first SMB extract stream. If DPA or DHA were present in the finished feed stream in line 62, then DPA and DHA also would be present in the first SMB extract stream in line 64. The first SMB raffinate stream in line 65 comprises fatty acid esters of OLE, LIN, and the polar and non-polar solvents such as heptane and ethyl acetate. The extract concentration of EPA in the first SMB extract stream in line 64 is enhanced relative to the feed concentration of EPA in the finished feed stream in line 62. The first extract stream in line 64 is passed to an first extract solvent recovery zone 216 to separate the esters from the solvents to provide a first solvent free extract stream, or an enhanced omega-3 ester product stream, in line 70 comprising the omega-3 fatty acid esters of EPA or DHA or mixtures thereof, and a first SMB1 recovered solvent stream in line 68, consisting of the non-polar solvent, heptane, and polar solvent, ethyl acetate. The first solvent free extract stream is essentially free of non-polar solvent having less than about 30 ppm non-polar solvent. Optionally, the first solvent free extract stream is passed to a further finishing zone (not shown) wherein the first solvent free extract stream is contacted with a silica adsorbent to substantially remove any remaining non-polar solvent from the first solvent free extract stream. The first primary raffinate stream in line 65 is passed to a first raffinate solvent recovery zone 218 to separate the ester phase comprising non-polar solvent and non-omega-3 components including fatty acid esters of LIN and OLE, from the non-polar solvent to provide a first SMB reject stream in line 66 and a second SMB1 recovered solvent stream in line 67, consisting of the non-polar solvent, heptane and ethyl acetate. The first reject stream in line 66 can be employed as a component of biodiesel or sent for further recovery of remaining fatty acid esters (Not shown). The solvent recovery zones 216 and 218 separate the solvent by evaporization or vacuum distillation. At least a portion of each of the first SMB1 recovered solvent stream in line 68 and the second SMB1 recovered solvent stream in line 67 are recycled to makeup a portion of the mobile phase desorbent stream in line 63 (not shown). The recovered solvent streams in lines 67 and 68 can be recycled to provide at least a portion of the non-polar solvent stream in line 50 (not shown). The first solvent free extract stream in line 70 and a second mobile phase desorbent stream in line 118 comprising a mixture of methanol and water are passed to a second SMB (simulated moving bed) zone 203. The second mobile phase desorbent stream has a ratio of methanol to water of about 93:7 on a volume basis. The second SMB zone 203 has a plurality of adsorbent beds (at least 8 adsorbent beds) containing a second stationary phase adsorbent and the adsorbent beds are arranged serially in a manner which is described hereinbelow in FIG. 3. The second stationary phase adsorbent is a hydrophobic C8 or C18 adsorbent. Preferably, the second stationary phase adsorbent is C18. A second SMB extract stream in line 120 is withdrawn from the second SMB zone 203 and passed to a second extract solvent recovery zone 204 to provide a second reject stream in line 126 and a first SMB2 recovered solvent stream in line 128. A second primary raffinate stream is withdrawn in line 122 and passed to a second raffinate solvent recovery zone 205 to provide a first evaporated raffinate stream in line 124 and a second SMB2 recovered solvent stream in line 130. At least a portion of each of the first SMB2 recovered solvent stream in line 128 and the second SMB2 recovered solvent stream in line 130 are recycled to makeup a portion of the second mobile phase desorbent stream in line 118 (not shown). The second reject stream in line 126 can be employed as a component of biodiesel or sent for further recovery of remaining fatty acid esters (not shown). The solvent recovery zones 204 and 205 separate the solvent by evaporization or vacuum distillation. The second evaporated raffinate stream as a third feed stream in line 124 and a third mobile phase desorbent stream in line 132 comprising a mixture of methanol and water are passed to a third SMB zone (SMB2) 206. The third mobile phase desorbent stream has a ratio of methanol to water of about 93:7 on a volume basis. The third SMB zone 206 has a plurality of adsorbent beds (at least 8 adsorbent beds) containing a third stationary phase adsorbent and arranged serially in a manner which is described hereinbelow in FIG. 3. The third stationary phase adsorbent is a hydrophobic C8 or C18 adsorbent. Preferably, the third stationary phase adsorbent is C18. A third SMB extract stream in line 134 is withdrawn from the third SMB zone and passed to an SMB3 extract solvent recovery zone 207 to provide a high purity EPA product stream in line 136 and a first SMB3 recovered solvent stream in line 140. A third primary raffinate stream is withdrawn from the third SMB zone 206 in line 142 and passed to an SMB3 raffinate solvent recovery zone 208 to provide a third evaporated raffinate stream in line 144 which represents a third reject stream, and a second SMB3 recovered solvent stream in line 146. At least a portion of each of the first SMB3 recovered solvent stream in line 140 and the second SMB3 recovered solvent stream in line 146 are recycled to makeup a portion of the desorbent stream in line 132. The third reject stream in line 144 can be employed as a component of biodiesel or sent for further recovery of remaining fatty acid esters (Not shown). The solvent recovery zones 207 and 208 separate the solvent by evaporization or vacuum distillation. The high purity EPA product stream in line 136 comprises an EPA concentration of greater than or equal to about 98 wt-% on a solvent free basis. The operation of the SMB2 and the SMB3 as individual SMB separation zones to recover EPA from crude fish oil streams using hydrophobic adsorbents and organic alcohol solvents as desorbents are disclosed in US Publication No. 2012/0330043.

Figure 3:
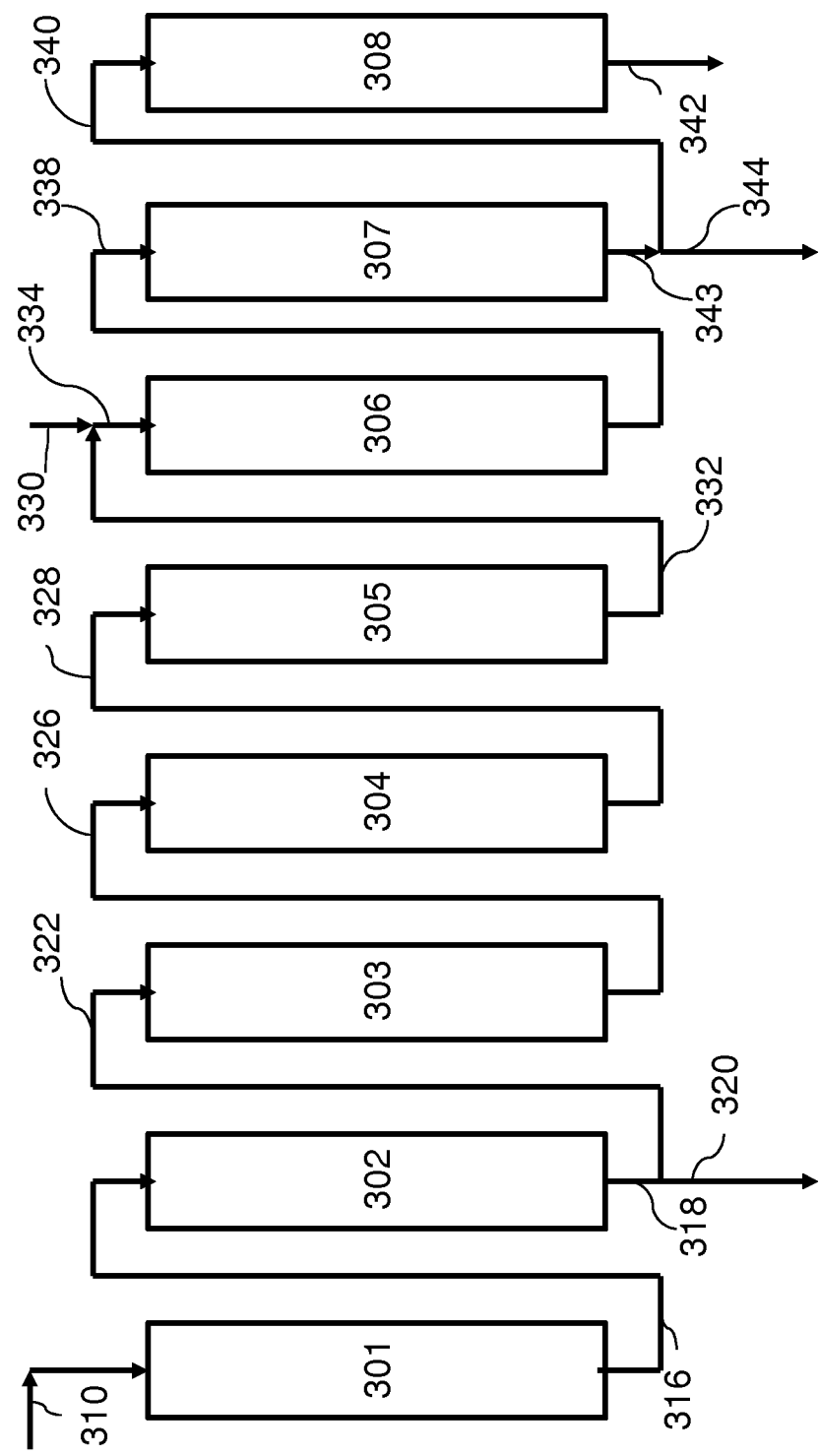
FIG. 3 is a schematic process flow diagram illustrating a configuration of the simulated moving bed cycle in one embodiment of the invention.

Referring to FIG. 3, one embodiment of the simulated moving bed zone of the present invention as used in each of the SMB zones described hereinabove is shown herein as operating in a simulated moving bed (SMB) cycle based on an eight adsorbent bed arrangement. Adsorbent beds 301, 302, 303, 304, 305, 306, 307, and 308, containing a stationary phase adsorbent as described hereinabove, are disposed in a serial configuration such that in accordance with a prearranged cycle, conduit 316 provides fluid communication between the bottom of adsorbent bed 301 with the top of adsorbent bed 302, conduits 318 and 322 provide fluid communication between the bottom of adsorbent bed 302 bed and the top of adsorbent bed 303, conduit 326 provides fluid communication between the bottom of adsorbent bed 303 with the top of adsorbent bed 304, conduit 328 provides fluid communication between the bottom of adsorbent bed 304 with the top of adsorbent bed 305, conduits 332 and 334 provide fluid communication between the bottom of adsorbent bed 305 with the top of adsorbent bed 306, conduit 338 provides fluid communication between the bottom of adsorbent bed 306 with the top of adsorbent bed 307, conduits 343 and 340 provide fluid communication between the bottom of adsorbent bed 307 with the top of adsorbent bed 308, and conduit 344 provides for the withdrawal of fluid from the bottom of adsorbent bed 307 as the primary raffinate, and line 342 provides for the withdrawal of a secondary raffinate or void volume flush of the adsorbent bed 308 which is in transition from the desorption zone to the adsorption zone. At least a portion of the secondary raffinate in line 342 can be used as desorbent and admixed with the desorbent stream in line 310 (not shown) to offset the demand for desorbent in the SMB process. According to the prearranged SMB cycle of the present invention, an SMB zone feed stream is passed to the SMB adsorption zone in line 330 and 334 to adsorbent bed 306. A primary raffinate stream is withdrawn from adsorbent bed 307 in conduits 343 and 344, and an extract stream is withdrawn via conduits 318 and 320 from adsorbent bed 302. A mobile phase desorbent stream as described hereinabove is introduced to adsorbent bed 301 in conduit 310. In this embodiment, the adsorbent beds 301-308 are indexed according to a 2-3-2-1 SMB cycle such that at least 2 adsorbent beds (301 and 302) undergo desorption in a desorption zone, at least 3 adsorbent beds (303, 304, and 305) undergo rectification in a rectification zone, and at least 3 adsorbent beds (306, 307, and 308) undergo adsorption in an adsorption zone during the SMB cycle of the present invention.

Alternatively, another embodiment of the invention can be carried out using a batch chromatographic bed following the esterification, transesterification and finishing steps described hereinabove. The batch chromatographic process comprises the following steps:

a. passing the finished feed stream through a chromatographic bed containing a silica adsorbent until a breakthrough of EPA occurred;

b. terminating the passing of the finished feed stream to the chromatographic bed and passing a non-polar solvent to the chromatographic bed and collecting a raffinate stream comprising non-polar solvent and LIN and OLE;

c. terminating the passing of the non-polar solvent to the chromatographic bed and passing a polar solvent to the chromatographic bed and collecting an extract stream; and, d. passing the extract stream to a polar solvent recovery zone to remove the polar solvent and recovering the enhanced omega-3 ester product, having a reduced amount of LIN and OLE relative to the finished feed stream.

This batch chromatographic separation process provides the ability of the silica adsorbent to perform the enrichment of the EPA component while significantly reducing the concentration of the OLE and LIN components in the extract stream by using a non-polar solvent as the loading solvent and a polar solvent as the desorbent solvent.

EXAMPLES

Example 1

Transesterification of Crude Fish Oil in Heptane

A 100 ml portion of a crude fish oil having 15 wt-% EPA, 7.7 wt-% DHA and 1.6 wt-% SDA as major components and the remainder components were saturated and unsaturated triglycerides was added to a 2 liter round bottom reaction vessel. 200 ml of ethanol (95 wt-%) and 250 ml of heptane were added to the reaction vessel and the reaction vessel contents were continuously stirred at a rate of 50 to 60 rotations per minute. 42 ml of a 1M sodium hydroxide solution in ethanol was added to the reaction vessel at ambient conditions including a room temperature of about 15° C. The 1M sodium hydroxide solution was prepared by crushing 40 grams of anhydrous sodium hydroxide to a powder and adding the powder to 1 liter of Reagent grade ethanol and stirring for an hour with intermediate shaking. The reaction vessel was stirred for about 100 minutes at room temperature, whereupon the reaction vessel contents were transferred to a distribution funnel. 500 ml of deionized water (DI) were added to the distribution funnel to wash the reactor effluent, and the contents of the distribution funnel were shaken and allowed to settle for about 150 minutes to achieve phase separation. The bottom layer, or water layer, was removed and a second wash water amount of 500 ml DI was added to the separation funnel, shaken, and allowed to again settle and phase separate. The second water formed was removed, and the wash step was repeated a third time with 1000 ml of DI water. The separation funnel was allowed to settle over night and the top layer, or ester layer was collected. Of the 100 ml of crude fish oil charged to the reaction vessel, 90 ml of transesterification effluent was recovered in the heptane phase. The weight recovery of the ester phase was 75 percent by weight.

Example 2

Reverse Phase SMB with 98:2 Heptane to Ethyl Acetate

The transesterification effluent of Example 1 comprising 90 ml of esterified crude fish oil in the 250 ml of heptane were diluted to provide a 10 wt-% feed stream by adding a sufficient amount of a 98:2 volume ratio of heptane:ethyl acetate solution. This diluted feed stream was charged to an 8 bed, simulated moving bed system, configured to operate in a 2-3-2-1 cycle (See FIG. 3). Each of the 8 adsorbent beds were 300 mm in length and 22 mm in diameter and filled with silica adsorbent having a particle size of 300-500 microns (Available from FUJI SILYSIA CHEMICAL LTD., Japan). The SMB columns were precondition with a desorbent containing a 98:2 volume ratio of heptane:ethyl acetate to remove any fines which may have been present. The following flow conditions established in the SMB system are shown in Table 1.

TABLE 1

Reverse Phase Flow Conditions of Example 2

| Stream | Flow Rate | Unit |
|---|---|---|
| Feed | 2.0 | ml/min |
| Desorbent | 37.5 | ml/min |
| Primary Raffinate | 16.0 | ml/min |
| Extract | 10.5 | ml/min |
| Secondary Raffinate | 13.0 | ml/min |

The SMB system was allowed to attain equilibrium and the extract stream and the primary raffinate stream were collected. The secondary raffinate stream was completely recycled (100%) to offset the desorbent stream demand. The extract stream and the primary raffinate stream were collected and the solvent in each stream was evaporated to provide 56 mg of primary raffinate and 16 mg of extract.

Analytical Methods:

The streams produced were analyzed in the following manner:

Triglyceride Analysis was carried out by HPLC. The HPLC was equipped with Reliasil ODS C18 column (250 mm×4.6 mm, and the C18 adsorbent had a particle size of 3 μm, (Available from Orochem Technologies Inc., IL, USA). The Reliasil column was maintained at 45° C., and eluted with an isocratic solvent system comprising 1:1 Acetone:Acetonitrile at 1.0 ml/min. The detection was made by a Waters 410 Differential Refractometer (Available from Waters-Milford, Mass.). Samples were dried to remove any solvent present and diluted into a 10% solution with Acetone. 20 ul injections were made for each sample. The peaks were detected using the RI and the resolved sample components were identified by comparison with peak retention times and calibration curves of standard components.

Ester Analysis was made by GC Analysis:

Ester samples were analyzed on a HP6890 GC (Available from Hewlett Packard). A DBWax column (Available from Agilent Technologies-Santa Clara, Calif.) was used for separation of the components in each sample. A gradient system was set up for the GC as shown in the Table below.

| Analysis | Ester Analysis | |
|---|---|---|
| Column | DBWax | Units |
| Dimension | 0.25 × 50 × 0.25 | mm × m × μm |
| Injection Port | | |
| Inlet Temp | 250 | ° C. |
| Injection | Split | |
| Split Ratio | 50-1 | |
| Total Flow | 161 | ml/min |
| Gradient setting | | |
| Oven Temp | | |
| Rate C/min | Temp ° C. | Stay Min |
| | 170 | 2 |
| 3 | 240 | 3 |
| Detector Port | | |
| Detector Temp | 270 | ° C. |
| Hydrogen Flow | 30 | ml/min |
| Air Flow | 400 | ml/min |
| Nitrogen Flow | 30 | ml/min |

Ester sample injections were carried out at 1 μl per sample with a 10 μl syringe.

HPLC Analysis:

HPLC was equipped with Reliasil C18 column (150 mm×4.6 mm, 5 μm Particle size)(Available from Orochem Technologies Inc., IL, USA). At 25° C., the HPLC column was eluted with isocratic solvent system of 100% methanol at a rate of 1.0 ml/min. The Reliasil C18 column was maintained at 25° C. The detection was made by a Waters 410 Differential Refractometer (Waters-Milford, Mass.). Samples were dried to remove any solvent present and made into a 10% solution with methanol. 20 ul injections were made for each sample. The peaks were detected using the RI and the resolved sample components were identified by comparison with peak retention times and calibration curves of standard components. The following conditions were employed for the HPLC:

| Analysis | Ester Analysis | |
|---|---|---|
| Column | Reliasil C30 | |
| Dimension | 250 × 4.6 | mm × mm |
| Desorbent | 98:2 - Methanol:Water | |
| Flow Rate | 1 | ml/min |
| Temperature | 25 | C. |
| Detection | RI | |

Figure 4:
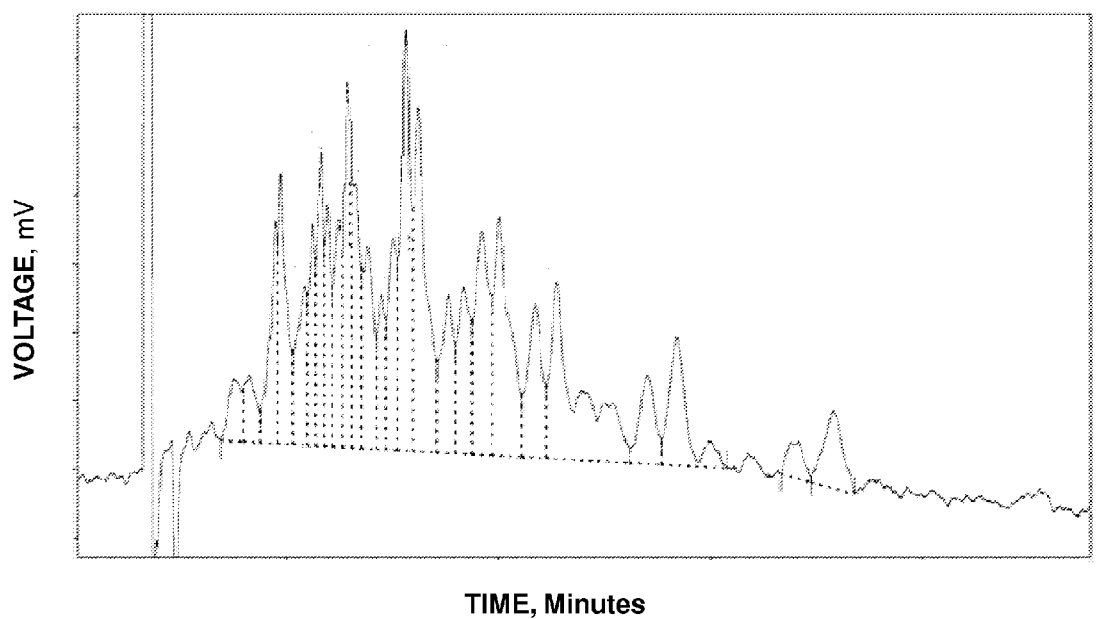
FIG. 4 is a composition trace produced by high pressure liquid chromatography (HPLC) analysis of a sample of crude fish oil.

The analytical results of Examples 1 and 2 were depicted in graphical form in the following figures:

FIG. 4 shows a composition trace produced by high pressure liquid chromatography (HPLC) analysis of a sample of crude fish oil showing the composition of the fish oil sample employed in Example 1.

Figure 5:
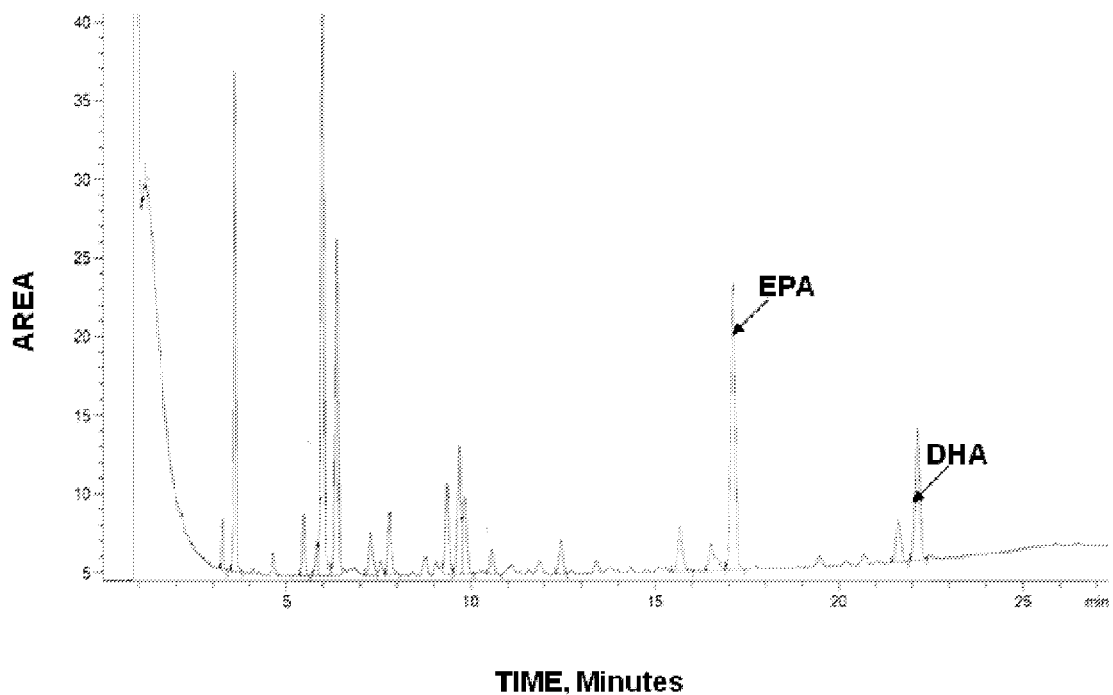
FIG. 5 is a gas chromatographic area plot of the ester layer showing the results of a composition analysis of the fish oil following an esterification step.

FIG. 5 shows the gas chromatographic area plot of the ester layer showing the results of a composition analysis of the fish oil following the above described esterification step of Example 1.

Figure 6:
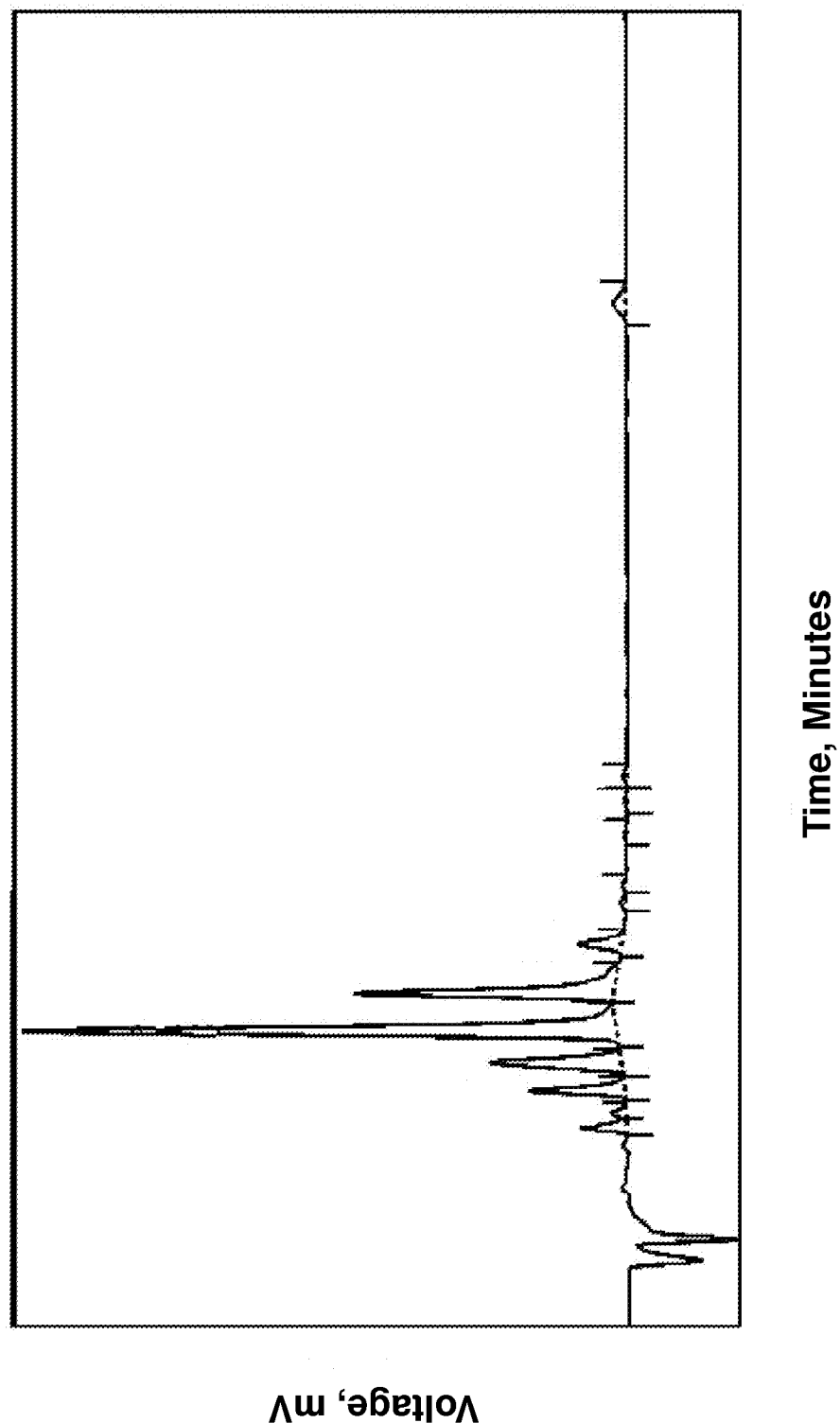
FIG. 6 is a composition tract produced by high pressure liquid chromatography (HPLC) analysis of a cumulative extract stream withdrawn from the SMB zone of the present invention.

FIG. 6 shows the composition tract produced by high pressure liquid chromatography (HPLC) analysis of a cumulative extract stream withdrawn from the SMB zone of the present invention as described in Example 2.

Figure 7:
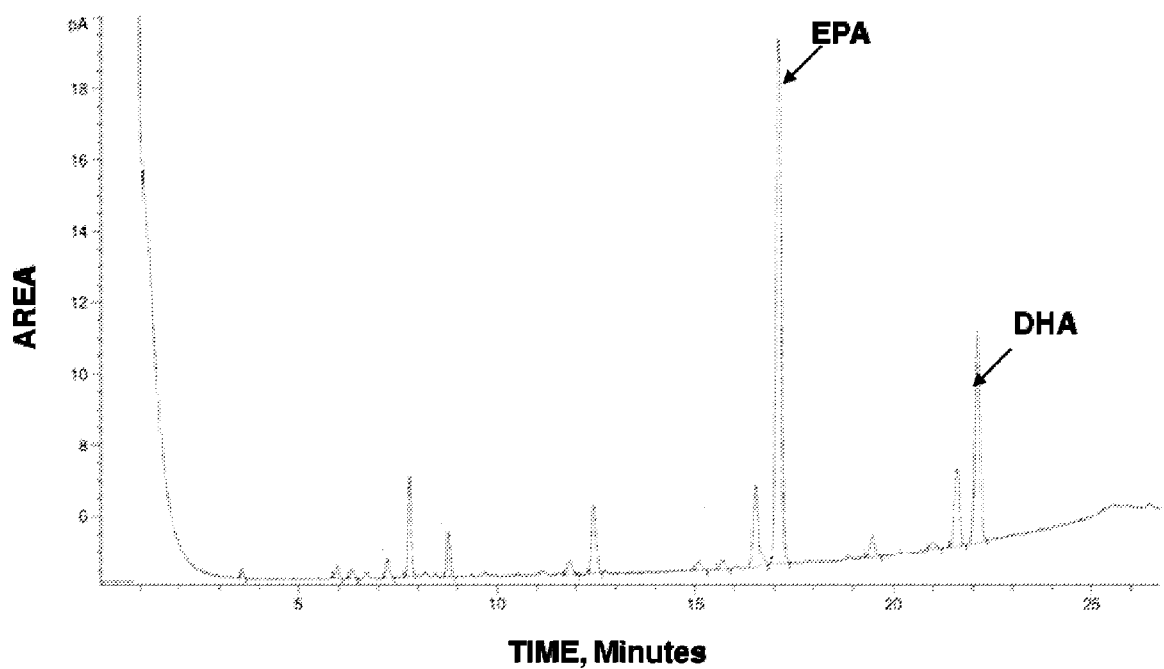
FIG. 7 is a gas chromatographic area plot showing the results of a composition analysis of the extract stream withdrawn from the SMB zone of the present invention.

FIG. 7 shows the gas chromatographic area plot showing the results of a composition analysis of the extract stream withdrawn from the SMB zone of Example 2.

Figure 8:
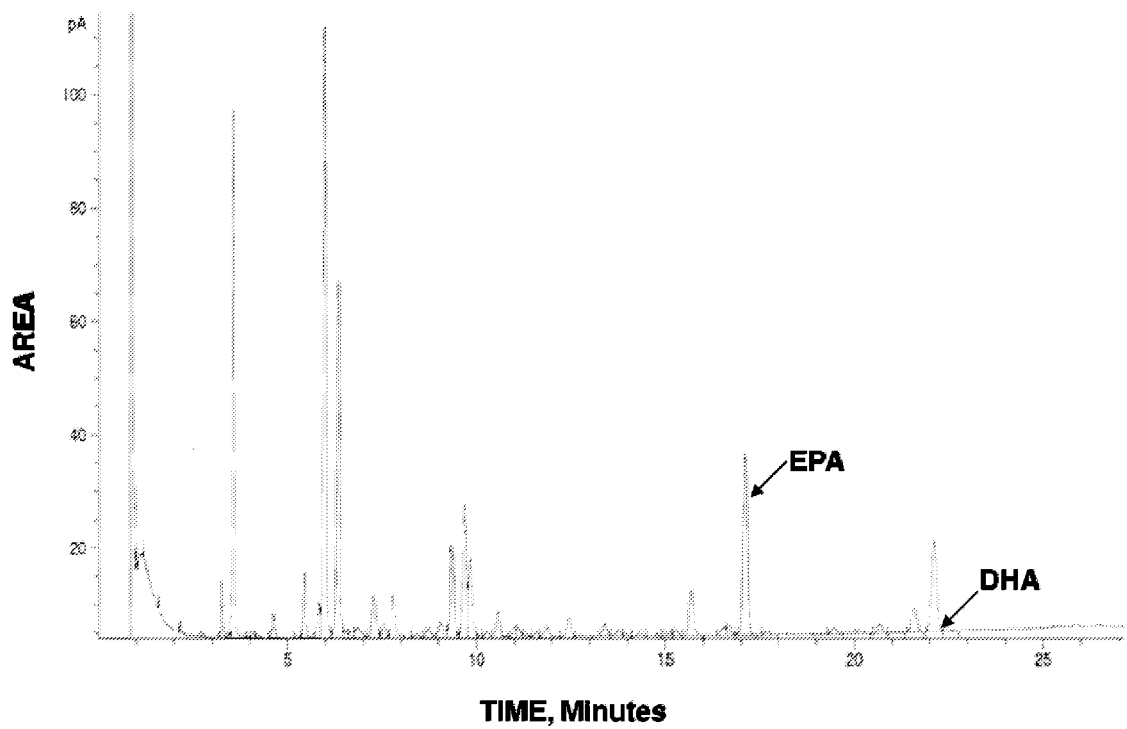
FIG. 8 is a gas chromatographic area plot showing the results of a composition analysis of the primary raffinate stream withdrawn from the first SMB zone of the present invention.

FIG. 8 shows the gas chromatographic area plot showing the results of a composition analysis of the primary raffinate stream withdrawn from the SMB zone of Example 2.

Example 3

Comparative Operation of Prior Art Process

A comparison of the operation of a complex for the production of a high purity EPA product was developed using actual experimental data for esterification of crude fish oil and the subsequent SMB processing steps. The results of the these experiments were combined with engineering calculations to show the impact on an overall material balance to a complex processing the same feed. The prior art Scheme A employed conventional esterification combined with a cascade of three SMB zones operating in a reverse phase mode using a hydrophobic C18 adsorbent and a polar desorbent comprising methanol:water as described hereinabove with reference to FIG. 1 to achieve an EPA purity of 95%. In the prior art scheme the three SMB cascade comprised:

SMB1—A C18 adsorbent system SMB using a 98:2 Methanol:Water as the desorbent. The SMB1 raffinate comprised an ester phase having an Omega-3 purity of from 85-90 wt-% (EPA+DHA). The SMB1 raffinate stream was evaporated to remove solvent to provide an evaporated SMB1 raffinate.

SMB2—The evaporated SMB1 raffinate was passed a second SMB zone, SMB2, comprising a C18 adsorbent system and using a desorbent comprising a 93:7 volume ratio of methanol:water. In SMB2, DHA ester is removed from the EPA ester in the SMB2 extract stream and an EPA enriched SMB2 raffinate stream, having an EPA content of about 94 wt-% in the ester phase of the SMB2 raffinate stream is produced. The SMB2 raffinate is evaporated to provide an evaporated SMB2 raffinate stream.

SMB3—The evaporated SMB2 raffinate was passed a third SMB zone, SMB3, comprising a C18 adsorbent system and using a desorbent comprising a 93:7 volume ratio of methanol:water. In this final SMB zone of the cascade, SDA ester is separated from the EPA. A C18 adsorbent bed SMB with 93:7 volume ratio of methanol:water to provide an extract stream having a 97 wt-% EPA concentration in the ester phase. After evaporation, a final ester product having a purity, less than 97 wt-%, of about 95 wt-% EPA is recovered as shown hereinbelow in Table 5.

Scheme B, the process of the instant invention, employed the two-phase, two step esterification of the instant invention combined with a cascade of three SMB zones, wherein the first SMB zone was a normal phase SMB operation employing a hydrophilic adsorbent comprising silica and a desorbent comprising a 98:2 volume ratio of heptane:ethyl acetate mixture, and the SMB2 and SMB3 zones are operated in a reversed phase as described hereinabove with reference to FIG. 2. Table 2 illustrates the key fatty acid ester components in the feed composition of the crude fish oil feed stream following esterification.

TABLE 2

EPA Ester Feed Stock Prior to SMB Cascade

| Feed composition | | EPA Ester Feed, wt-% |
|---|---|---|
| C18:1 | OLE | 3.8 |
| C18:2 | LIN | 5.53 |
| C18:3 | ALA | 0.57 |
| C18:4 | SDA | 1.34 |
| C20:4 | ETA | 0.55 |
| C20:5 | EPA | 12.22 |
| C22:5 | DPA | 1.98 |
| C22:6 | DHA | 5.68 |
| Total | | 27.87 |

The following tables contrast the operation of Scheme A and Scheme B by showing the intermediate composition of high value EPA containing stream after each SMB stage in the cascade. Table 3 shows the composition of the first primary raffinate stream from scheme A compared to the first extract stream from Scheme B.

TABLE 3

Comparison of EPA Rich Effluent after Stage 1

| Feed composition | | Scheme A, wt-% | Scheme B, wt-% |
|---|---|---|---|
| C18:1 | OLE | 0.1 | 0 |
| C18:2 | LIN | 0.1 | 0 |
| C18:3 | ALA | 0.7 | 1.1 |
| C18:4 | SDA | 2.0 | 4.6 |
| C20:4 | ETA | 0.5 | 6.08 |
| C20:5 | EPA | 40.0 | 38.5 |
| C22:5 | DPA | 1.5 | 6.36 |
| C22:6 | DHA | 4.5 | 16.09 |
| Total | | 49.4 | 72.13 |
| EPA Yield | Wt-% | 80 | 95 |

The first primary raffinate stream in Scheme A retains a small amount of OLE and LIN impurities and represents only and 80 wt-% recovery of the EPA component in the feed. In Scheme B, the inventive scheme, essentially all of the OLE and LIN impurities are removed and the overall recovery of the EPA is 95 wt-%. The presence of the LIN and OLE constrain the separation and reduce throughput.

After the second SMB zone, the EPA rich streams again show a significant difference in the recovery and purification of the EPA component. Table 4 shows the second primary raffinate of Scheme A and the second primary raffinate stream of Scheme B. The purity of the EPA in the second primary raffinate in Scheme B has increased to 94 wt-%, while the EPA purity in the second primary raffinate stream in the prior art Scheme A is at 90 wt-%.

TABLE 4

Comparison of EPA Rich Primary Raffinates after Stage 2

| Feed composition | | Scheme A, wt-% | Scheme B, wt-% |
|---|---|---|---|
| C18:1 | OLE | 0.1 | 0 |
| C18:2 | LIN | 0.1 | 0 |
| C18:3 | ALA | 0.6 | 0.6 |
| C18:4 | SDA | 2.0 | 2.8 |
| C20:4 | ETA | 0.2 | 0.2 |
| C20:5 | EPA | 90.0 | 94.0 |
| C22:5 | DPA | 0 | 0 |
| C22:6 | DHA | 0.2 | 0.2 |
| Total | | 93.0 | 97.8 |
| EPA Yield | Wt-% | 80 | 80 |

After the third SMB zone, the difference in the EPA purity between the Scheme A and Scheme B is more clearly defined.

The purity of the EPA derived from Scheme A is 95 wt-%, while the purity of the third extract stream in Scheme B has increased to about 99 wt-% on a solvent free basis. Table 5 shows the EPA yield and purity of the third SMB extract stream on a solvent free basis. The improvement in the EPA purity of the final product of Scheme B is attributed to the removal of OLE and LIN from the first extract stream from the normal phase SMB.

TABLE 5

Comparison of EPA Rich Primary Raffinates after Stage 2

| Feed composition | | Scheme A, wt-% | Scheme B, wt-% |
|---|---|---|---|
| C18:1 | OLE | 0.1 | 0 |
| C18:2 | LIN | 0.1 | 0 |
| C18:3 | ALA | 0.5 | 0.2 |
| C18:4 | SDA | 0.3 | 0.3 |
| C20:4 | ETA | 0.2 | 0.3 |
| C20:5 | EPA | 95.0 | 98.8 |
| C22:5 | DPA | 0 | 0 |
| C22:6 | DHA | 0.2 | 0.3 |
| Total | | 96.4 | 99.9 |
| EPA Yield | Wt-% | 98 | 98 |

Thus, on an overall complex basis, Scheme B of the present invention achieved a higher purity and a high recovery of the EPA component from the same feed. On the basis of an overall material balance, for a complex processing 2 metric tonnes of fish oil in Scheme A would produce about 1.25 metric tonnes of 95 wt-% EPA product, while Scheme B would produce 1.5 metric tonnes of 99 wt-% EPA product.

Example 4

Effect of Molecular Distillation on EPA

Molecular distillation causes the EPA to form isomers due to the high intensity heat the esters have to endure. The table below compares the isomer content of typical prior art fish oil feed stocks comprising EPA after molecular distillation (EPA60 and EPA70) with the isomer content of the feed stocks prepared according to the present invention by esterification and transesterification in a non-polar solvent for use in the normal phase SMB zone. No isomers of EPA are produced in either the feed preparation step or the normal phase SMB zone of the present invention. The presence of the A, B, C, D, and E isomers of EPA in the feed stock cannot be separated from the EPA product recovered, and thus limit the purity of the final product by the amount of the isomers in the final product. As shown hereinbelow, the EPA 60 and the EPA 70 contain about 1% impurity compared to the process of the present invention which contains essentially no isomers.

TABLE 6

Comparison of Molecular Distillation Feed Stocks and Feed Stock Prepared According to the Present Invention

| Feed composition | | Existing Feed Samples | | EPA feed used for NP Process | |
|---|---|---|---|---|---|
| | | EPA60 | EPA70 | EPA ester feed | EPA SMB Extract |
| EPA + EPA ISOMERS | ISO-A | 0.34 | 0.35 | 0 | 0 |
| | EPA | 58.66 | 69.97 | 12.98 | 43.5 |
| | ISO-B | 0.14 | 0.14 | 0 | 0 |

TABLE 6-continued

Comparison of Molecular Distillation Feed Stocks and Feed Stock Prepared According to the Present Invention

| Feed composition | | Existing Feed Samples | | EPA feed used for NP Process | |
|---|---|---|---|---|---|
| | | EPA60 | EPA70 | EPA ester feed | EPA SMB Extract |
| | ISO-C | 0.29 | 0.09 | 0 | 0 |
| | ISO-D,E | 0.72 | 0.3 | 0 | 0 |
| Sum of Isomer | | 1.49 | 0.88 | 0 | 0 |

Example 5

Batch Mode—Silica Adsorbent

A sample of esterified crude fish oil, esterified according to the instant invention, having about 12 wt-% EPA was diluted with heptane to provide a feed stream having 10 wt-% fish oil in the non-polar solvent, heptane. A packed single chromatographic bed of stainless steel having a length of 300 mm and an inside diameter of 22 mm was filled with 65 grams of a silica adsorbent having a particle size ranging from 40 to 63 microns. The feed stream was passed through the single chromatographic bed until EPA breakthrough occurred. The EPA breakthrough occurred after passing about 600 ml of the feed stream to the single chromatographic bed. The feed stream passing was stopped and five bed volumes (575 ml) of heptane were passed through the single chromatographic bed to flush out all of the non-adsorbed components to provide a raffinate stream. A polar solvent, ethanol (99%), was then passed through the single chromatographic bed to desorb the adsorbed components and recover the extract stream. The composition of the feed stream and the extract stream are shown hereinbelow on a solvent free basis in Table 7.

TABLE 7

GC Analysis of Feed and Ethanol Extract Streams—Batch Separation

| | | Feed | Extract |
|---|---|---|---|
| C18:1 | OLE | 3.8 | 0.16 |
| C18:2 | LIN | 5.53 | 1.6 |
| C18:3 | ALA | 0.57 | 0.9 |
| C18:4 | SDA | 1.34 | 3.2 |
| C20:4 | ETA | 0.55 | 4.2 |
| C20:5 | EPA | 12.22 | 28.74 |
| C22:5 | DPA | 1.98 | 4.3 |
| C22:6 | DHA | 5.68 | 13.03 |

This batch chromatographic separation proves the ability of the silica adsorbent to perform the enrichment of the EPA component while significantly reducing the concentration of the OLE and LIN components in the extract stream by using a non-polar solvent as the loading solvent and a polar solvent as the desorbent solvent.

Although the systems and processes described herein have been described in detail, it should be understood that various changes, substitutions, and alterations can be made without departing from the spirit and scope of the invention as defined by the following claims. Those skilled in the art may be able to study the preferred embodiments and identify other ways to practice the invention that are not exactly as described herein. It is the intent of the inventors that variations and equivalents of the invention are within the scope of the claims, while the description, abstract and drawings are not to be used to limit the scope of the invention. The invention is specifically intended to be as broad as the claims below and their equivalents.

We claim:

1. A process for recovering an enhanced omega-3 ester product from a crude fish oil comprising fatty acids of omega-3 fatty acids of eicosapentaenoic acid (EPA) or docosahexaenoic acid (DHA) along with other unsaturated triglyceride species including at least one of docosapentanoic acid (DPA), stearadonic acid (SDA), alpha linolenic acid (ALA), gamma linolenic acid (GLA), linoleic acid (LIN) and oleic acid (OLE) and free fatty acids, said process comprising:

a. passing the crude fish oil to a solvent mixing zone and therein admixing the crude fish oil with a non-polar solvent to provide a fish oil/solvent mixture;

b. passing the fish oil/solvent mixture to an esterification zone and therein subjecting the fish oil/solvent mixture to an esterification reaction in the presence of an ethanol stream and an acid catalyst stream comprising a mineral acid at effective esterification conditions to convert the free fatty acids to Fatty Acid Ethyl Esters (FAEE) to provide a non-polar esterification reaction effluent stream comprising non-polar solvent, fatty acids of omega-3 fatty acids of EPA or DHA or mixtures of EPA and DHA, and said unsaturated triglyceride species, and a polar esterification reaction phase comprising ethanol, water, the FAEE, and said mineral acid;

c. admixing the non-polar esterification reaction effluent stream with a polar solvent stream to form a transesterification reaction feed stream and passing the transesterification feed stream to a transesterification zone and subjecting the transesterification feed stream to a transesterification reaction in the presence of a basic catalyst stream at effective transesterification reaction conditions to convert the fatty acids of omega-3 fatty acids of EPA or DHA to omega-3 fatty acid esters comprising EPA or DHA or mixtures of EPA and DHA, and to convert the unsaturated triglycerides to glycerol and to other fatty acid ethyl esters of LIN, OLE and at least one of DPA, SDA, ALA, and GLA to provide a two-phase transesterification reaction effluent stream;

d. passing the two-phase transesterification reaction effluent stream to a wash/separation zone and therein washing the two-phase transesterification reaction effluent stream with water, stabilizing, and phase separating the two-phase transesterification reaction effluent stream to provide an aqueous phase stream comprising the polar solvent, water and glycerol, and a non-polar transesterification effluent stream comprising water, non-polar solvent, omega-3 fatty acid esters and said other fatty acid esters of LIN, OLE and at least one of DPA, SDA, ALA, and GLA;

e. finishing the non-polar transesterification effluent stream to remove water in a finishing zone to provide a finished feed stream comprising non-polar solvent, omega-3 fatty acid esters and other fatty acid esters;

f. passing the finished feed stream and a mobile phase desorbent to a normal phase simulated moving bed adsorption (SMB) zone, said normal phase SMB zone containing a hydrophilic stationary phase agent, said normal phase SMB zone comprising a plurality of adsorbent beds and operating in an effective normal phase cycle, said mobile phase desorbent comprising a non-polar solvent and an organic polar solvent in an effective normal phase solvent ratio to provide a first SMB extract stream, a primary SMB raffinate stream, and a secondary SMB raffinate stream a portion of which is recycled to provide at least a portion of the mobile phase desorbent, said SMB extract stream comprising non-polar solvent and omega-3 fatty acid esters and other fatty acid esters of at least one of DPA, SDA, ALA, and GLA and being essentially free of OLE and LIN, said primary SMB raffinate stream comprising non-polar solvent and fatty acid esters of OLE and LIN;

g. passing the first SMB extract stream to a first extract solvent recovery zone and therein recovering the non-polar solvent to provide the enhanced omega-3 ester product comprising EPA or DHA or mixtures thereof being essentially free of OLE and LIN and having and EPA purity of greater than 97 wt-% EPA and a first SMB recovered solvent stream comprising the non-polar solvent, and passing the primary SMB raffinate stream to a raffinate solvent recovery zone and therein recovering the non-polar solvent to provide an SMB reject stream and a second SMB recovered solvent stream comprising the non-polar solvent and the polar organic solvent; and, h. returning at least a portion of the first SMB recovered solvent stream and the second SMB recovered solvent stream to be admixed with the mobile phase desorbent.

2. The process of claim 1, wherein the wherein the fish oil/solvent mixture has a ratio of 2 to 3 parts non-polar solvent to 1 part crude fish oil.

3. The process of claim 1, wherein the effective esterification conditions include an esterification temperature of 25° C. or less.

4. The process of claim 1, wherein the mineral acid is sulfuric acid.

5. The process of claim 1, wherein the effective transesterification reaction conditions include a transesterification reaction temperature which is at or below a room temperature of 25° C. and the transesterification reaction zone is continuously stirred.

6. The process of claim 1, wherein the basic catalyst comprises a base metal hydroxide dissolved in ethanol.

7. The process of claim 1, wherein the polar solvent is methanol, ethanol, or propanol.

8. The process of claim 1, wherein the non-polar solvent is hexane or heptane.

9. The process of claim 1, wherein the mobile phase desorbent is a mixture of the non-polar solvent consisting of heptane or hexane and the organic polar solvent consists of ethyl acetate and the effective normal phase solvent ratio is from about 95:5 to 99 parts non-polar solvent to 5 to 1 parts polar organic solvent.

10. The process of claim 1, wherein the mobile phase desorbent is a mixture of heptane or hexane and ethyl acetate and the effective normal phase solvent ratio is 98 parts heptane or hexane to 2 parts ethyl acetate.

11. The process of claim 1, wherein the SMB zone comprises at least eight adsorbent beds and the effective normal phase cycle comprises a 2-3-2-1 SMB cycle such that at least 2 adsorbent beds undergo desorption in a desorption zone, at least 3 adsorbent beds undergo rectification in a rectification zone, and at least 3 adsorbent beds undergo adsorption in an adsorption zone.

12. The process of claim 1, wherein the SMB zone comprises at least eight adsorbent beds containing silica as the hydrophilic stationary phase agent.

13. The process of claim 1, wherein the finishing zone comprises a silica adsorbent.

14. A process for preparing a high purity EPA product from a crude fish oil comprising a crude fish oil comprising fatty acids of omega-3 fatty acids of eicosapentaenoic acid (EPA) or docosahexaenoic acid (DHA) along with other unsaturated triglyceride species including at least one of docosapentanoic acid (DPA), stearadonic acid (SDA), alpha linolenic acid (ALA), gamma linolenic acid (GLA), linoleic acid (LIN) and oleic acid (OLE) and free fatty acids, said process comprising:

a. passing the crude fish oil to a solvent mixing zone and therein admixing the crude fish oil with a non-polar solvent to provide a fish oil/solvent mixture;

b. passing the fish oil/solvent mixture to an esterification zone and therein subjecting the fish oil/solvent mixture to an esterification reaction in the presence of an ethanol stream and an acid catalyst stream comprising a mineral acid at effective esterification conditions to convert the free fatty acids to Fatty Acid Ethyl Esters (FAEE) to provide a non-polar esterification reaction effluent stream comprising non-polar solvent, fatty acids of omega-3 fatty acids of EPA or DHA or mixtures of EPA and DHA, and said unsaturated triglyceride species, and a polar esterification reaction phase comprising ethanol, water, the FAEE, and said mineral acid;

c. admixing the non-polar esterification reaction effluent stream with a polar solvent stream to form a transesterification reaction feed stream and passing the transesterification feed stream to a transesterification zone and subjecting the transesterification feed stream to a transesterification reaction in the presence of a basic catalyst stream at effective transesterification reaction conditions to convert the fatty acids of omega-3 fatty acids of EPA or DHA to omega-3 fatty acid esters comprising EPA or DHA or mixtures of EPA and DHA, and to convert the unsaturated triglycerides to glycerol and to other fatty acid ethyl esters of LIN, OLE and at least one of DPA, SDA, ALA, and GLA to provide a two-phase transesterification reaction effluent stream;

d. passing the two-phase transesterification reaction effluent stream to a wash/separation zone and therein washing the two-phase transesterification reaction effluent stream with water, stabilizing, and phase separating the two-phase transesterification reaction effluent stream to provide an aqueous phase stream comprising the polar solvent, water and glycerol, and a non-polar transesterification effluent stream comprising water, non-polar solvent, omega-3 fatty acid esters and said other fatty acid esters of LIN, OLE and at least one of DPA, SDA, ALA, and GLA;

e. finishing the non-polar transesterification effluent stream to remove water in a finishing zone to provide a finished feed stream comprising non-polar solvent, omega-3 fatty acid esters and other fatty acid esters;

f. passing the filtered feed stream and a first stage mobile phase desorbent to a normal phase simulated moving bed adsorption (SMB) zone, said normal phase SMB zone containing a hydrophilic stationary phase agent, said normal phase SMB zone comprising a plurality of adsorbent beds and operating in an effective normal phase cycle, said first stage mobile phase desorbent comprising a non-polar solvent and an organic polar solvent in an effective first stage solvent ratio to provide a first SMB extract stream, a first primary SMB raffinate stream, and a first secondary SMB raffinate stream which is recycled to provide at least a portion of the first stage mobile phase desorbent, said first SMB extract stream comprising non-polar solvent and omega-3 fatty acid esters and other fatty acid esters of at least one DPA, SDA, ALA, and GLA and being essentially free of OLE and LIN, said first primary SMB raffinate stream comprising non-polar solvent and fatty acid esters of OLE and LIN;

g. passing the first SMB extract stream to a first extract solvent recovery zone and therein recovering the non-polar solvent to provide a first extract stream and a first SMB1 recovered solvent stream comprising the non-polar solvent, and passing the first primary raffinate stream to a first raffinate solvent recovery zone and therein recovering the non-polar solvent to provide a first SMB reject stream and a second SMB recovered solvent stream comprising the non-polar solvent the first extract solvent and admixing at least a portion of the first and second SMB recovered solvent stream with the first stage mobile phase desorbent;

h. diluting the first extract stream with an effective amount of a polar solvent and counter-currently passing the diluted first extract stream and a second stage mobile phase desorbent to a first reverse phase simulated moving bed adsorption (SMB) zone, said first reverse phase SMB zone containing hydrophobic stationary phase agent, said first reverse phase SMB zone comprising a plurality of adsorbent beds and operating in an effective reverse phase cycle, said second stage mobile phase desorbent comprising a polar solvent and water in an effective second stage solvent ratio to provide a second SMB extract stream, a second primary SMB raffinate stream, and a second secondary SMB raffinate stream which is recycled to provide at least a portion of the second stage mobile phase desorbent, said second primary SMB raffinate stream comprising polar solvent and fatty acid esters of EPA, said second primary SMB raffinate stream comprising polar solvent and fatty acid ester of DHA, and other fatty acid esters of at least one DPA, SDA, ALA, and GLA;

i. passing the second primary SMB raffinate stream to a second raffinate solvent recovery zone and therein recovering the polar solvent to provide a second raffinate stream and a first SMB2 recovered solvent stream comprising the polar solvent, and passing the second extract stream to a second extract solvent recovery zone and therein recovering the polar solvent to provide a second SMB reject stream and a second SMB2 recovered solvent stream comprising the non-polar solvent the first extract solvent;

j. diluting the second raffinate stream with an effective amount of the polar solvent and counter-currently passing the diluted second raffinate stream and a third stage mobile phase desorbent to a third simulated moving bed (SMB) zone, said third SMB zone containing hydrophobic stationary phase agent, said third SMB zone comprising a plurality of adsorbent beds, said third stage mobile phase desorbent comprising a polar solvent and water in an effective third stage solvent ratio to provide a third SMB extract stream, a third primary SMB raffinate stream, and a third secondary SMB raffinate stream which is recycled to provide at least a portion of the third stage mobile phase desorbent, said third primary SMB raffinate stream comprising polar solvent and fatty acid esters of DHA and other fatty acid esters of at least one DPA, SDA, ALA, and GLA, said third SMB extract stream comprising polar solvent and fatty acid ester of EPA; and, k. passing the third primary SMB raffinate stream to a third raffinate solvent recovery zone and therein recovering the polar solvent to provide a third SMB reject stream and a first SMB3 recovered solvent stream comprising the polar solvent, and passing the third extract stream to a third extract solvent recovery zone and therein recovering the polar solvent to provide a high purity EPA product stream being essentially free of OLE and LIN having an EPA purity greater than 97 wt-% EPA and a second SMB3 recovered solvent stream comprising the polar solvent the first extract solvent.

15. The process of claim 14, wherein the fish oil/solvent mixture has a ratio of 2 to 3 parts solvent to 1 part fish oil.

16. The process of claim 14, wherein the high purity EPA product comprises an EPA purity of greater than 99 wt-% EPA.

17. The process of claim 14, wherein the first extract stream is essentially free of ethyl esters of OLE and LIN.

18. The process of claim 14, wherein the non-polar solvent is hexane or heptane.

19. The process of claim 14, wherein the first stage mobile phase desorbent is a mixture of heptane or hexane and ethyl acetate and the effective normal phase solvent ratio is 98 parts heptane or hexane to 2 parts ethyl acetate.

20. The process of claim 14, wherein at least a portion of the first SMB reject stream, the second SMB reject stream, and third SMB reject stream are recovered as a biodiesel stream.

21. A batch process for recovering an enhanced omega-3 ester product from a crude fish oil comprising fatty acids of omega-3 fatty acids of eicosapentaenoic acid (EPA) or docosahexaenoic acid (DHA) along with other unsaturated triglyceride species including at least one of docosapentanoic acid (DPA), stearadonic acid (SDA), alpha linolenic acid (ALA), gamma linolenic acid (GLA), linoleic acid (LIN) and oleic acid (OLE) and free fatty acids, said process comprising:
   a. passing the crude fish oil to a solvent mixing zone and therein admixing the crude fish oil with a non-polar solvent to provide a fish oil/solvent mixture;
   b. passing the fish oil/solvent mixture to an esterification zone and therein subjecting the fish oil/solvent mixture to an esterification reaction in the presence of an ethanol stream and an acid catalyst stream comprising a mineral acid at effective esterification conditions to convert the free fatty acids to Fatty Acid Ethyl Esters (FAEE) to provide a non-polar esterification reaction effluent stream comprising non-polar solvent, fatty acids of omega-3 fatty acids of EPA or DHA or mixtures of EPA and DHA, and said unsaturated triglyceride species, and a polar esterification reaction phase comprising ethanol, water, the FAEE, and said mineral acid;
   c. admixing the non-polar esterification reaction effluent stream with a polar solvent stream to form a transesterification reaction feed stream and passing the transesterification feed stream to a transesterification zone and subjecting the transesterification feed stream to a transesterification reaction in the presence of a basic catalyst stream at effective transesterification reaction conditions to convert the fatty acids of omega-3 fatty acids of EPA or DHA to omega-3 fatty acid esters comprising EPA or DHA or mixtures of EPA and DHA, and to convert the unsaturated triglycerides to glycerol and to other fatty acid ethyl esters of LIN, OLE and at least one of DPA, SDA, ALA, and GLA to provide a two-phase transesterification reaction effluent stream;
   d. passing the two-phase transesterification reaction effluent stream to a wash/separation zone and therein washing the two-phase transesterification reaction effluent stream with water, stabilizing, and phase separating the two-phase transesterification reaction effluent stream to provide an aqueous phase stream comprising the polar solvent, water and glycerol, and a non-polar transesterification effluent stream comprising water, non-polar solvent, omega-3 fatty acid esters and said other fatty acid esters of LIN, OLE and at least one of DPA, SDA, ALA, and GLA;
   e. finishing the non-polar transesterification effluent stream to remove water in a finishing zone to provide a finished feed stream comprising non-polar solvent, omega-3 fatty acid esters and other fatty acid esters;
   f. passing the finished feed stream through a chromatographic bed containing a hydrophilic silica adsorbent until a breakthrough of EPA occurred;
   g. terminating the passing of the finished feed stream to the chromatographic bed and passing a non-polar solvent to the chromatographic bed and collecting a raffinate stream comprising non-polar solvent and LIN and OLE;
   h. terminating the passing of the non-polar solvent to the chromatographic bed and passing a polar solvent to the chromatographic bed and collecting an extract stream; and,
   i. passing the extract stream to a polar solvent recovery zone to remove the polar solvent and recovering the enhanced omega-3 ester product, having an EPA purity greater than 97 wt-% EPA and being essentially free of LIN and OLE.

22. The process of claim 1, wherein the crude fish oil is a mixture of triglycerides comprising fatty acids of omega-3 fatty acids of eicosapentaenoic acid (EPA) or docosahexaenoic acid (DHA) along with other unsaturated triglyceride species including at least one of docosapentanoic acid (DPA), stearadonic acid (SDA), alpha linolenic acid (ALA), gamma linolenic acid (GLA), linoleic acid (LIN) and oleic acid (OLE) and free fatty acids.

23. The process of claim 1, wherein the effective esterification conditions include an esterification temperature of 40° C. or less.

* * * * *